(12) United States Patent
Keaney et al.

(10) Patent No.: US 11,744,823 B2
(45) Date of Patent: Sep. 5, 2023

(54) PHARMACEUTICAL COMPOSITIONS OF A SELECTIVE C-KIT KINASE INHIBITOR AND METHODS FOR MAKING AND USING SAME

(71) Applicant: Third Harmonic Bio, Inc., Cambridge, MA (US)

(72) Inventors: Gregg F. Keaney, Lexington, MA (US); Elizabeth Kwong, Montreal (CA)

(73) Assignee: Third Harmonic Bio, Inc., Cambridge, MA (US)

( * ) Notice: Subject to any disclaimer, the term of this patent is extended or adjusted under 35 U.S.C. 154(b) by 0 days.

(21) Appl. No.: 17/455,739

(22) Filed: Nov. 19, 2021

(65) Prior Publication Data
US 2022/0184045 A1    Jun. 16, 2022

Related U.S. Application Data

(60) Provisional application No. 63/203,675, filed on Jul. 28, 2021, provisional application No. 63/115,690, filed on Nov. 19, 2020.

(51) Int. Cl.
*A61K 31/437*     (2006.01)
*A61K 9/16*       (2006.01)

(52) U.S. Cl.
CPC .............. *A61K 31/437* (2013.01); *A61K 9/16* (2013.01)

(58) Field of Classification Search
CPC .......... A61K 31/437; A61P 9/12; A61P 29/00; C12Q 1/001
USPC ....................................................... 514/300
See application file for complete search history.

(56) References Cited

U.S. PATENT DOCUMENTS

| | | | |
|---|---|---|---|
| 4,475,323 A | 10/1984 | Schwartzberg et al. | |
| 4,475,725 A | 10/1984 | Niemann | |
| 5,086,018 A | 2/1992 | Conru et al. | |
| 6,028,570 A | 2/2000 | Gilger et al. | |
| 8,569,283 B2 | 10/2013 | Molteni et al. | |
| 8,569,583 B2 | 10/2013 | Donovan et al. | |
| 8,754,071 B2 | 6/2014 | Molenti et al. | |
| 9,023,839 B2 | 5/2015 | Molteni et al. | |
| 9,199,981 B2 | 12/2015 | Yeh et al. | |
| 2007/0072862 A1 | 3/2007 | Dimauro et al. | |
| 2012/0297717 A1 | 11/2012 | Keller et al. | |
| 2013/0023751 A1 | 1/2013 | Lichtenstein et al. | |
| 2013/0059832 A1 | 3/2013 | Molteni et al. | |
| 2013/0059846 A1 | 3/2013 | Yeh et al. | |
| 2014/0031333 A1 | 1/2014 | Molenti et al. | |
| 2014/0228347 A1 | 8/2014 | Molteni et al. | |
| 2015/0011508 A1 | 1/2015 | Liu et al. | |
| 2015/0051206 A1 | 2/2015 | Loren et al. | |
| 2022/0056026 A1 | 2/2022 | Keaney et al. | |

FOREIGN PATENT DOCUMENTS

| | | | | |
|---|---|---|---|---|
| WO | WO-2006027795 A1 | 3/2006 | | |
| WO | WO-2006071940 A2 | 7/2006 | | |
| WO | WO-2007022380 A2 | 2/2007 | | |
| WO | WO-2008058037 A1 | 5/2008 | | |
| WO | WO-2011113606 A1 | 9/2011 | | |
| WO | WO-2012143796 A2 | 10/2012 | | |
| WO | WO 2013/033070 A1 * | 3/2013 | ........... | C07D 471/04 |
| WO | WO-2013033070 A1 | 3/2013 | | |
| WO | WO-2013033116 A1 | 3/2013 | | |
| WO | WO-2013033167 A1 | 3/2013 | | |
| WO | WO-2013033203 A1 | 3/2013 | | |
| WO | WO-2013033620 A1 | 3/2013 | | |
| WO | WO-2018140796 A1 | 8/2018 | | |
| WO | WO 2020/228746 A1 * | 11/2020 | ........... | C07D 471/04 |
| WO | WO-2020228746 A1 | 11/2020 | | |
| WO | WO-2022016021 A1 | 1/2022 | | |

OTHER PUBLICATIONS

Babaei et al., "Receptor tyrosine kinase (c-Kit) inhibitors: a potential therapeutic target in cancer cells," Drug Des Devel Ther. 2016; 10:2443-59.

Caira, M.R., "Crystalline Polymorphism of Organic Compounds." Design of Organic Solids. Topics in Current Chemistry. 1998:198;163-208.

Database Registry, Chemical Abstracts Service, Columbus, Ohio, US, Apr. 14, 2011, XP002685983, Database accession No. 1280077-39-5, N-[3-(3-cycolopropyl-1H-1,2,4-triazol-5-yl)phenyl ]-5-methylimidazo[1,2-a]pyridine-2-carboxamide.

Database Registry, Chemical Abstracts Service, Columbus, Ohio, US, Mar. 14, 2010, XP002685990, Database accession No. 1209616-10-3, N-[3-[6-[(4-morpholinyl)-3-pyridazinyl]phenyl-2-methylimidazo[1,2-a]pyridine-3-carboxamide.

International Search Report and Written Opinion issued by the European Patent Office, as International Searching Authority, for International Patent Application No. PCT/US2012/052621, dated Nov. 13, 2012 (10 pages).

International Search Report and Written Opinion issued by the European Patent Office, as International Searching Authority, for International Patent Application No. PCT/US2012/052802, dated Nov. 8, 2012 (10 pages).

International Search Report and Written Opinion issued by the National Intellectual Property Administration, PRC, as International, Searching Authority for International Patent Application No. PCT/CN2019/086582, dated Jan. 23, 2020 (15 pages).

International Search Report and Written Opinion issued by the National Intellectual Property Administration, PRC, as International, Searching Authority for International Patent Application No. PCT/CN2020/090060, dated Aug. 12, 2020 (14 pages).

(Continued)

*Primary Examiner* — Charanjit Aulakh
(74) *Attorney, Agent, or Firm* — Dechert LLP; Andrea L. C. Reid; Chad E. Davis

(57) ABSTRACT

The present disclosure relates generally to pharmaceutical compositions of N-(5-(5-((1R,2S)-2-fluorocyclopropyl)-1,2,4-oxadiazol-3-yl)-2-methylphenyl)imidazo[1,2-a]pyridine-3-carboxamide useful as a selective inhibitor of c-kit kinase and uses of the same in the treatment of c-kit kinase associated diseases.

12 Claims, 8 Drawing Sheets

(56) References Cited

OTHER PUBLICATIONS

International Search Report and Written Opinion issued by the National Intellectual Property Administration, PRC, as International, Searching Authority for International Patent Application No. PCT/CN2020/102095, dated Apr. 16, 2021 (18 pages).

International Search Report and Written Opinion issued by the United States Patent and Trademark Office as International Searching Authority for International Patent Application No. PCT/US2021/041903, dated Oct. 28, 2021 (9 pages).

Kim et al., "Design and Synthesis of Imidazopyridine Analogues as Inhibitors of Phosphoinositide 3-Kinase Signaling and Angiogenesis," J Med Chem. 2011; 54(7):2455-2466.

Morphy, "Selectively Nonselective Kinase Inhibition: Striking the Right Balance," J Med Chem. 2010; 53(4):1413-1437.

PCT International Search Report and Written Opinion from PCT/EP2021/082295 dated Feb. 23, 2022.

PCT International Search Report and Written Opinion from PCT/US2021/072503 dated Feb. 16, 2022.

Pecharsky and Zavalij, "Fundamentals of Powder Diffraction and Structural Charaterization of Materials," Kluwer Academic Publishers. 2003.

Pubchem, N-(5-(5-((1 R,2S)-2-Fluorocyclopropyl)-1 2,4-oxadiazol-3-yl)-2-methylphenyl)imidazo[1,2-a]pyridine-3-carboxamide, CID 71280305, Mar. 21, 2013, modified Sep. 25, 2021 (13 pages). Available at: https://pubchem.ncbi.nlm.gov/compound/71280305.

Pubchem, N-[5-[5-(2-Fluorocyclopropyl)-1,2,4-oxadiazol-3-yl]-2-methylphenyl]imidazo[1,2-a]pyridine-3-carboxamide, CID 78048019, Sep. 25, 2014, modified Sep. 25, 2021 (8 pages). Available at: https://pubchem.ncbi.nlm.gov/compound/78048019.

Roskoski, "The role of small molecule Kit protein-tyrosine kinase inhibitors in the treatment of neoplastic disorders," Pharmacol Res. 2018; 133:35-52.

U.S. Department of Health and Human Services et al., "Regulatory Classification of Pharmaceutical Co-Crystals: Guidance for Industry," Draft Guidance. Aug. 2016;Revision 1.

\* cited by examiner

PHARMACEUTICAL COMPOSITIONS OF A SELECTIVE C-KIT KINASE INHIBITOR AND METHODS FOR MAKING AND USING SAME

CROSS REFERENCE TO RELATED APPLICATIONS

This application claims the benefit of U.S. Provisional Application No. 63/115,690, filed Nov. 19, 2020, and U.S. Provisional Application No. 63/203,675, filed Jul. 28, 2021, the entirety of each of which is incorporated herein by reference.

FIELD OF THE INVENTION

The present disclosure relates generally to pharmaceutical compositions of N-(5-(5-((1R,2S)-2-fluorocyclopropyl)-1,2,4-oxadiazol-3-yl)-2-methylphenyl)imidazo[1,2-a]pyridine-3-carboxamide useful as a selective inhibitor of c-kit kinase and uses of the same in the treatment of c-kit kinase associated diseases.

BACKGROUND

N-(5-(5-((1R,2S)-2-fluorocyclopropyl)-1,2,4-oxadiazol-3-yl)-2-methylphenyl)imidazo[1,2-a]pyridine-3-carboxamide, first disclosed in WO 2013/033070 A1, is a selective inhibitor of c-kit kinase, useful for the depletion of mast cells and thus is useful for treating mast-cell associated diseases including asthma, allergic rhinitis, pulmonary arterial hypertension (PAH), pulmonary fibrosis, hepatic fibrosis, cardiac fibrosis, scleroderma, irritable bowel syndrome (IBS), inflammatory bowel disease (IBD), urticaria, dermatosis, atopic dermatitis, allergic contact dermatitis, rheumatoid arthritis, multiple sclerosis, melanoma, a gastrointestinal stromal tumor, a mast cell tumor, mastocytosis, anaphylactic syndrome, food allergy, type I diabetes and type II diabetes.

There remains a need in the art for novel compositions for delivering c-kit kinase inhibitors and methods for treating c-kit associated diseases using the same.

SUMMARY OF THE INVENTION

It has now been found that pharmaceutical compositions of the present disclosure, and compositions thereof, are useful for administering a selective inhibitor of c-kit kinase to a patient in need thereof and exhibit desirable characteristics for the same. In general, the pharmaceutically acceptable compositions disclosed herein are useful for treating or lessening the severity of a variety of diseases or disorders as described in detail herein.

DETAILED DESCRIPTION OF THE INVENTION

Figure 1A:
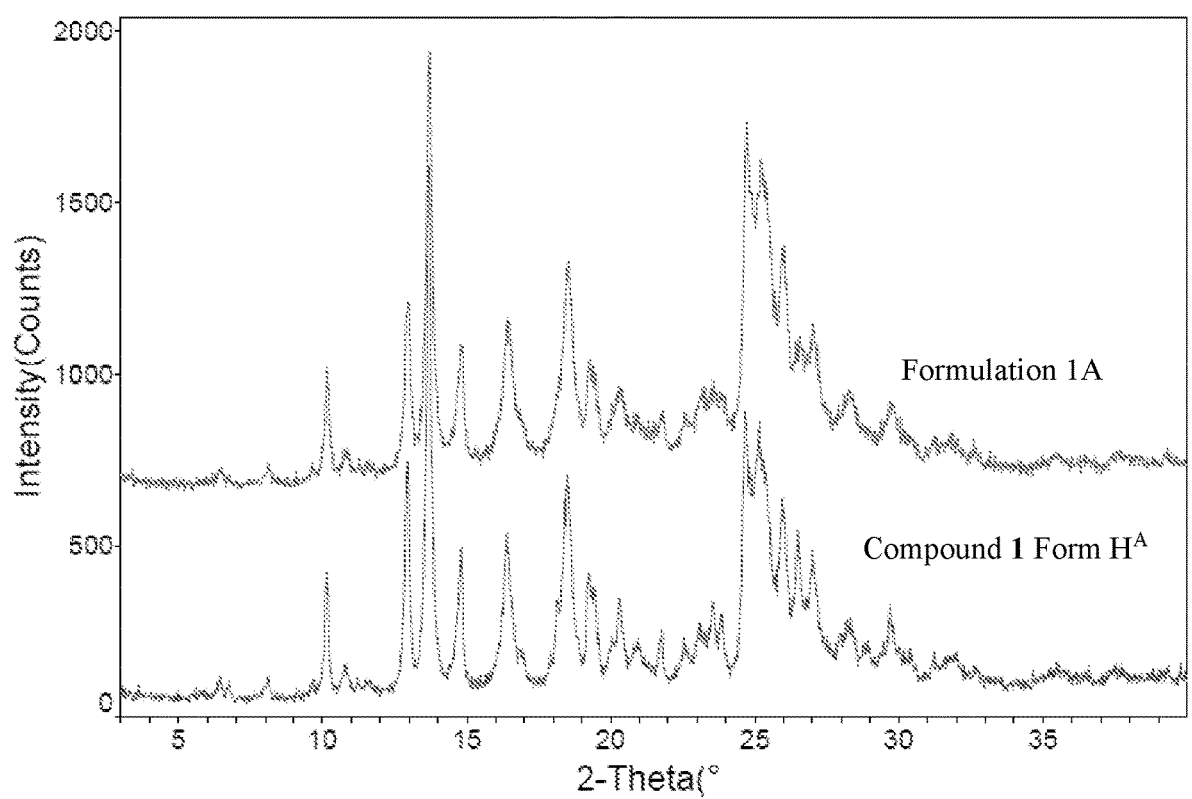
FIG. 1A depicts XRPD patterns for Formulation 1A, as compared to Compound 1 Form $H^A$ starting material.

The present disclosure is based at least in part on the identification of a compound that modulates c-kit kinase and methods of using the same to treat c-kit kinase associated diseases. Disclosed herein is Compound 1, and pharmaceutical compositions thereof:

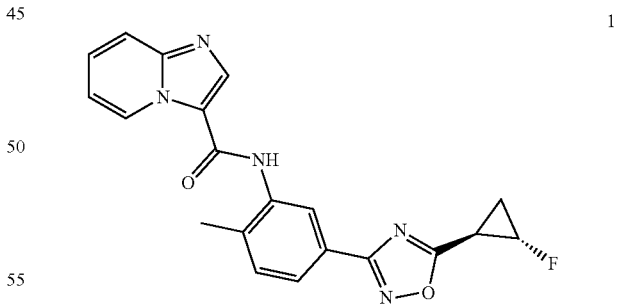

1

Compound 1, N-(5-(5-((1R,2S)-2-fluorocyclopropyl)-1,2,4-oxadiazol-3-yl)-2-methylphenyl)imidazo[1,2-a]pyridine-3-carboxamide, is active in a variety of assays and therapeutic models, acting as a selective inhibitor of c-kit kinase.

It would be desirable to provide pharmaceutically acceptable compositions comprising Compound 1 (e.g., as a free-base thereof or salt thereof) that imparts characteristics such as improved stability, improved oral bioavailability, and low toxicity risk. Accordingly, the present disclosure provides pharmaceutical compositions of Compound 1.

Micronized Blend Powdered Compositions:

In one aspect, the present invention provides a pharmaceutical composition for oral administration of Compound 1 to a subject, wherein Compound 1 is formulated as part of a micronized powder. In some embodiments, the pharmaceutical composition of the present invention comprises, or consists essentially of:

(i) Compound 1;

(ii) an acidulant;

(iii) a surfactant; and optionally one or more of: a filler, a disintegrant, a lubricant, a glidant, a stabilizer, a coloring agent, a sweetener and a flavorant. In some embodiments, the pharmaceutical composition comprises one, or more than one of any of the aforementioned components. For example, in some embodiments, the composition comprises two or more surfactants.

A. Compound 1

As defined above, a pharmaceutical composition of the present invention is a micronized powder comprising Compound 1. Compound 1 can be prepared according to example F110 of WO 2013/033070 A1, which is incorporated by reference herein, as summarized in the Scheme 1 provided below:

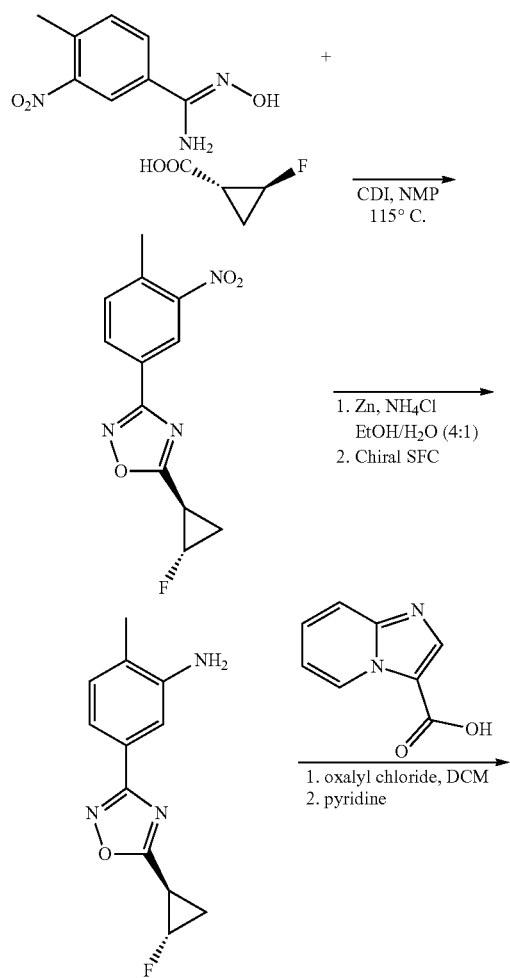

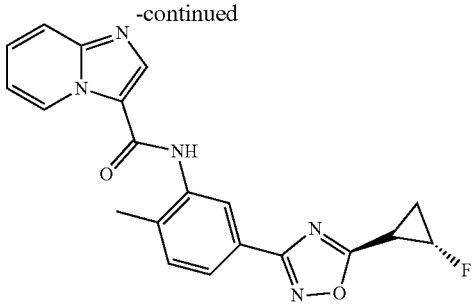

In some embodiments, the pharmaceutical composition is a micronized powder comprising dry microparticles of Compound 1. In some embodiments the microparticles of Compound 1 comprise amorphous Compound 1. In some embodiments, the microparticles of Compound 1 comprise a crystalline solid form of Compound 1. In some embodiments, the microparticles of Compound 1 comprise a crystalline free base solid form of Compound 1. In some embodiments, the microparticles of Compound 1 comprise a crystalline salt solid form of Compound 1.

In some embodiments, the crystalline solid form of Compound 1 is an anhydrate form. In some embodiments, the crystalline solid form of Compound 1 is a hydrate form. In some embodiments, the crystalline solid form of Compound 1 is a monohydrate. In some embodiments, the crystalline solid form of Compound 1 is a hemihydrate. In some embodiments, the crystalline solid form of Compound 1 is a dihydrate.

In some embodiments, the microparticles of Compound 1 comprise a crystalline solid form of Compound 1 disclosed in PCT/CN2020/090060, which is incorporated by reference herein.

In some embodiments, the microparticles of Compound 1 comprise free base Form A of Compound 1. In some embodiments, the microparticles of Compound 1 consist of free base Form A of Compound 1. In some embodiments, Form A of Compound 1 is a form having at least 1, 2, 3, 4 or 5 X-ray powder diffraction spectral peak(s) selected from the peaks listed in Table A below.

TABLE A

XRPD Peak Positions for Form A of Compound 1

| Position (°2θ) | Intensity % |
| --- | --- |
| 5.0 | 11.2 |
| 8.8 | 7.6 |
| 9.8 | 29.3 |
| 10.1 | 17.5 |
| 11.4 | 3.2 |
| 13.2 | 59.7 |
| 15.2 | 100 |
| 17.1 | 17.3 |
| 17.4 | 19.4 |
| 17.6 | 14.4 |
| 18.5 | 9.3 |
| 19.7 | 68.7 |

In this and all subsequent tables, the position (°2θ) is within ± 0.2.

In some embodiments, Form A of Compound 1 is characterized in that it has one or more peaks in its X-ray powder diffraction pattern selected from those at about 13.2, about 15.2, and about 19.7 degrees 2-theta. In some embodiments, Form A of Compound 1 is characterized in that it has two or more peaks in its X-ray powder diffraction pattern selected from those at about 13.2, about 15.2, and about 19.7 degrees 2-theta. In some embodiments, Form A of Compound 1 is characterized in that it has three peaks in its X-ray powder diffraction pattern at about 13.2, about 15.2, and about 19.7 degrees 2-theta. In some embodiments, Form A of Compound 1 is characterized by a DSC thermogram having an endothermic event at about 175° C. In some embodiments, Form A of Compound 1 is characterized by a TGA curve showing insignificant mass loss up to a temperature of about 180° C.

Form A can be isolated by the following procedure: Dissolve about 2.0 g of amorphous Compound 1 in 40 mL of isopropanol at 70° C. and mechanically stir for 3 hours. Cool the solution to room temperature and continue stirring overnight. A precipitate forms overnight and is filtered and washed with isopropanol and dried overnight at 60° C. under vacuum to yield Form A of Compound 1.

In some embodiments, the microparticles of Compound 1 are substantially pure. In some embodiments, the microparticles of Compound 1 comprise free base Form A and are substantially free of amorphous Compound 1 and other crystalline forms of Compound 1. As used herein, the term "substantially free" means that the compound contains no significant amount of amorphous Compound 1 or other crystalline forms. In certain embodiments, the microparticles comprise at least about 95% by weight of crystalline Compound 1 Form A. In some embodiments of the disclosure, the microparticles comprise at least about 99% by weight of crystalline Compound 1 Form A.

In some embodiments, the microparticles of Compound 1 comprise free base Form $H^4$ of Compound 1. In some embodiments, the microparticles of Compound 1 consist of free base Form $H^4$ of Compound 1. In some embodiments, Form $H^4$ of Compound 1 is a form having at least 1, 2, 3, 4 or 5 X-ray powder diffraction spectral peak(s) selected from the peaks listed in Table B below.

TABLE B

XRPD Peak Positions for Form $H^4$ of Compound 1

| Position (°2θ) | Intensity % |
| --- | --- |
| 6.4 | 12.4 |
| 8.0 | 4.0 |
| 10.1 | 2.2 |
| 10.7 | 10.4 |
| 12.8 | 100 |
| 13.6 | 37.0 |
| 16.3 | 3.3 |
| 16.8 | 8.0 |
| 18.4 | 7.0 |
| 19.3 | 27.1 |
| 19.9 | 11.3 |
| 21.6 | 2.9 |
| 25.6 | 8.7 |
| 26.9 | 3.5 |
| 32.6 | 3.2 |

In this and all subsequent tables, the position (°2θ) is within ± 0.2.

In some embodiments, Form $H^4$ of Compound 1 is characterized in that it has one or more peaks in its X-ray powder diffraction pattern selected from those at about 12.8, about 13.6, and about 19.3 degrees 2-theta. In some embodiments, Form $H^4$ of Compound 1 is characterized in that it has two or more peaks in its X-ray powder diffraction pattern selected from those at about 12.8, about 13.6, and about 19.3 degrees 2-theta. In some embodiments, Form $H^4$ of Compound 1 is characterized in that it has three peaks in its X-ray powder diffraction pattern at about 12.8, about 13.6, and about 19.3 degrees 2-theta. In some embodiments, Form $H^4$ of Compound 1 is characterized by a DSC thermogram having one or more endothermic events at temperatures selected from about 87° C., about 125° C., about 165° C. and about 175° C. In some embodiments, Form $H^4$ of Compound 1 is characterized by a TGA curve showing about a 5% mass loss up to a temperature of about 112° C.

Form $H^4$ can be isolated by the following procedure: Add about 200 mg of Form A of Compound 1 to 3.0 mL of MeOH/$H_2O$ (1:1, v/v) and stir at 1000 rpm at room temperature for 5 days. Centrifuge the suspension, collect the solids and dry under vacuum to yield Form $H^4$ of Compound 1.

In some embodiments, the microparticles of Compound 1 are substantially pure. In some embodiments, the microparticles of Compound 1 comprise free base Form $H^4$ and are substantially free of amorphous Compound 1 and other crystalline forms of Compound 1. In certain embodiments, the microparticles comprise at least about 95% by weight of crystalline Compound 1 Form $H^4$. In some embodiments of the disclosure, the microparticles comprise at least about 99% by weight of crystalline Compound 1 Form $H^4$.

In some embodiments, the microparticles of Compound 1 comprise free base Form $H^B$ of Compound 1. In some embodiments, the microparticles of Compound 1 consist of free base Form $H^B$ of Compound 1. In some embodiments, Form $H^B$ of Compound 1 is a form having at least 1, 2, 3, 4 or 5 X-ray powder diffraction spectral peak(s) selected from the peaks listed in Table C below.

TABLE C

XRPD Peak Positions for Form $H^B$ of Compound 1

| Position (°2θ) | Intensity % |
| --- | --- |
| 6.7 | 32.2 |
| 10.1 | 27.0 |
| 10.7 | 24.1 |
| 11.2 | 13.3 |
| 13.6 | 100 |
| 16.5 | 15.4 |
| 18.0 | 73.3 |
| 19.1 | 56.6 |
| 20.2 | 24.0 |
| 23.5 | 35.1 |
| 23.8 | 45.8 |
| 25.0 | 42.4 |
| 26.4 | 54.7 |
| 28.7 | 19.3 |
| 29.7 | 34.5 |

In this and all subsequent tables, the position (°2θ) is within ± 0.2.

In some embodiments, Form $H^B$ of Compound 1 is characterized in that it has one or more peaks in its X-ray powder diffraction pattern selected from those at about 13.6, about 18.0, and about 26.4 degrees 2-theta. In some embodiments, Form $H^B$ of Compound 1 is characterized in that it has two or more peaks in its X-ray powder diffraction pattern selected from those at about 13.6, about 18.0, and about 26.4 degrees 2-theta. In some embodiments, Form $H^B$ of Compound 1 is characterized in that it has three peaks in its X-ray powder diffraction pattern at about 13.6, about 18.0, and about 26.4 degrees 2-theta. In some embodiments, Form $H^B$ of Compound 1 is characterized by a DSC thermogram having one or more endothermic events at temperatures selected from about 110° C., about 125° C., about 165° C. and about 173° C. In some embodiments, Form $H^B$ of Compound 1 is characterized by a TGA curve showing about a 5.4% mass loss up to a temperature of about 150° C.

Form H$^B$ can be isolated by the following procedure: Add about 10 mg of Form A of Compound 1 to a vial of water and leave at room temperature for two weeks. Centrifuge the suspension, collect the solids and dry under vacuum to yield Form H$^B$ of Compound 1.

In some embodiments, the microparticles of Compound 1 are substantially pure. In some embodiments, the microparticles of Compound 1 comprise free base Form H$^B$ and are substantially free of amorphous Compound 1 and other crystalline forms of Compound 1. In certain embodiments, the microparticles comprise at least about 95% by weight of crystalline Compound 1 Form H$^B$. In some embodiments of the disclosure, the microparticles comprise at least about 99% by weight of crystalline Compound 1 Form H$^B$.

In some embodiments, the microparticles of Compound 1 comprise free base Form D of Compound 1. In some embodiments, the microparticles of Compound 1 consist of free base Form D of Compound 1. In some embodiments, Form D of Compound 1 is a form having at least 1, 2, 3, 4 or 5 X-ray powder diffraction spectral peak(s) selected from the peaks listed in Table D below.

TABLE D

XRPD Peak Positions for Form D of Compound 1

| Position (°2θ) | Intensity % |
|---|---|
| 3.1 | 14.1 |
| 5.1 | 8.8 |
| 8.9 | 34.7 |
| 9.9 | 80.7 |
| 10.2 | 9.5 |
| 11.4 | 4.8 |
| 13.3 | 71.7 |
| 15.3 | 46.3 |
| 17.2 | 90.7 |
| 17.7 | 61.8 |
| 18.6 | 28.2 |
| 19.8 | 100.0 |
| 20.4 | 10.6 |
| 21.3 | 2.5 |
| 22.1 | 17.2 |
| 22.9 | 10.8 |
| 24.6 | 3.9 |
| 26.1 | 28.0 |
| 26.9 | 4.2 |
| 27.6 | 5.1 |
| 27.9 | 2.5 |
| 29.9 | 2.4 |
| 31.4 | 2.2 |
| 32.0 | 0.8 |
| 33.0 | 1.5 |
| 34.3 | 2.0 |
| 34.7 | 2.0 |

In this and all subsequent tables, the position (°2θ) is within ± 0.2.

In some embodiments, Form D of Compound 1 is characterized in that it has one or more peaks in its X-ray powder diffraction pattern selected from those at about 8.9, about 9.9, about 13.3, about 15.3, about 17.2, about 17.7, about 19.8, about 26.1 degrees 2-theta. In some embodiments, Form D of Compound 1 is characterized in that it has two or more peaks in its X-ray powder diffraction pattern selected from those at about 8.9, about 9.9, about 13.3, about 15.3, about 17.2, about 17.7, about 19.8, about 26.1 degrees 2-theta. In some embodiments, Form D of Compound 1 is characterized in that it has three or more peaks in its X-ray powder diffraction pattern selected from those at about 8.9, about 9.9, about 13.3, about 15.3, about 17.2, about 17.7, about 19.8, about 26.1 degrees 2-theta. In some embodiments, Form D of Compound 1 is characterized in that it has four or more peaks in its X-ray powder diffraction pattern selected from those at about 8.9, about 9.9, about 13.3, about 15.3, about 17.2, about 17.7, about 19.8, about 26.1 degrees 2-theta. In some embodiments, Form D of Compound 1 is characterized in that it has five or more peaks in its X-ray powder diffraction pattern selected from those at about 8.9, about 9.9, about 13.3, about 15.3, about 17.2, about 17.7, about 19.8, about 26.1 degrees 2-theta. In some embodiments, Form D of Compound 1 is characterized in that it has six or more peaks in its X-ray powder diffraction pattern selected from those at about 8.9, about 9.9, about 13.3, about 15.3, about 17.2, about 17.7, about 19.8, about 26.1 degrees 2-theta. In some embodiments, Form D of Compound 1 is characterized in that it has seven or more peaks in its X-ray powder diffraction pattern selected from those at about 8.9, about 9.9, about 13.3, about 15.3, about 17.2, about 17.7, about 19.8, about 26.1 degrees 2-theta. In some embodiments, Form D of Compound 1 is characterized in that it has eight peaks in its X-ray powder diffraction pattern at about 8.9, about 9.9, about 13.3, about 15.3, about 17.2, about 17.7, about 19.8, about 26.1 degrees 2-theta. In some embodiments, Form D of Compound 1 is characterized by a DSC thermogram having an endothermic event at about 175° C. In some embodiments, Form D of Compound 1 is characterized by a TGA curve showing minimal mass loss up to a temperature of about 250° C.

Form D can be isolated by the following procedure: Add about 200 mg of Form A of Compound 1 to 3.0 mL of isopropanol and stir at 1000 rpm at room temperature for 5 days. Centrifuge the suspension, collect the solids and dry under vacuum to yield Form D of Compound 1.

In some embodiments, the microparticles of Compound 1 are substantially pure. In some embodiments, the microparticles of Compound 1 comprise free base Form D and are substantially free of amorphous Compound 1 and other crystalline forms of Compound 1. In certain embodiments, the microparticles comprise at least about 95% by weight of crystalline Compound 1 Form D. In some embodiments of the disclosure, the microparticles comprise at least about 99% by weight of crystalline Compound 1 Form D.

In some embodiments, the microparticles of Compound 1 comprise HCl salt Form I of Compound 1. In some embodiments, the microparticles of Compound 1 consist of HCl salt Form I of Compound 1. In some embodiments, Form I of Compound 1 HCl salt is an anhydrate form having a molar ratio of HCl to Compound 1 of about 1:1. In some embodiments, Form I of Compound 1 HCl salt is an anhydrate form having a molar ratio of HCl to Compound 1 of about 0.85:1. In some embodiments, Form I of Compound 1 HCl salt is a form having at least 1, 2, 3, 4 or 5 X-ray powder diffraction spectral peak(s) selected from the peaks listed in Table E below.

TABLE E

XRPD Peak Positions for Form I of Compound 1 HCl salt

| Position (°2θ) | Intensity % |
|---|---|
| 6.0 | 22.4 |
| 10.8 | 31.2 |
| 11.3 | 6.2 |
| 11.9 | 15.0 |
| 12.8 | 28.5 |
| 15.0 | 12.2 |
| 16.4 | 2.1 |
| 17.4 | 6.6 |
| 17.9 | 75.2 |
| 18.1 | 25.6 |
| 19.3 | 18.1 |

TABLE E-continued

XRPD Peak Positions for Form I of Compound 1 HCl salt

| Position (°2θ) | Intensity % |
|---|---|
| 20.2 | 18.1 |
| 21.7 | 11.6 |
| 22.5 | 4.0 |
| 23.5 | 4.7 |
| 24.0 | 7.0 |
| 25.6 | 76.7 |
| 26.5 | 100 |
| 27.7 | 3.8 |
| 29.0 | 10.3 |
| 30.0 | 2.3 |
| 31.5 | 2.6 |
| 32.9 | 2.6 |
| 34.4 | 1.5 |
| 38.0 | 1.8 |
| 39.2 | 1.0 |

In this and all subsequent tables, the position (°2θ) is within ± 0.2.

In some embodiments, Form I of Compound 1 HCl salt is characterized in that it has one or more peaks in its X-ray powder diffraction pattern selected from those at about 17.9, about 25.6 and about 26.5 degrees 2-theta. In some embodiments, Form I of Compound 1 HCl salt is characterized in that it has two or more peaks in its X-ray powder diffraction pattern selected from those about 17.9, about 25.6 and about 26.5 degrees 2-theta. In some embodiments, Form I of Compound 1 HCl salt is characterized in that it has three peaks in its X-ray powder diffraction pattern at about 17.9, about 25.6 and about 26.5 degrees 2-theta. In some embodiments, Form I of Compound 1 HCl salt is characterized by a DSC thermogram having an endothermic event at about 258.6° C. In some embodiments, Form I of Compound 1 HCl salt is characterized by a TGA curve showing minimal mass loss up to a temperature of about 150° C.

Form I can be isolated by the following procedure: Add about 2 g of Compound 1 free base to 20 mL of isopropanol in a first vial and stir to obtain a suspension. Add about 250 mg HCl (36 wt %) to 20 mL of isopropanol in a second vial to obtain a solution. Add the contents of the second vial to the first vial and stir (500 rpm) at room temperature for 3 days. Filter the contents of the vial and dry the solid under vacuum at room temperature overnight to yield Form I of Compound 1 HCl salt. Alternative solvents can also be used in place of the isopropanol, including ethanol.

In some embodiments, the microparticles of Compound 1 HCl salt Form I are substantially pure. In some embodiments, the microparticles of Compound 1 comprise HCl salt Form I and are substantially free of amorphous Compound 1 and other crystalline forms of Compound 1. In certain embodiments, the microparticles comprise at least about 95% by weight of crystalline Compound 1 HCl salt Form I. In some embodiments of the disclosure, the microparticles comprise at least about 99% by weight of crystalline Compound 1 HCl salt Form I.

In some embodiments, the microparticles of Compound 1 comprise fumaric acid salt Form J of Compound 1. In some embodiments, the microparticles of Compound 1 consist of fumaric acid salt Form of Compound 1. Form J of Compound 1 is an anhydrate form having a molar ratio of fumaric acid to Compound 1 of about 0.5:1. In some embodiments, Form J of Compound 1 is a form having at least 1, 2, 3, 4 or 5 X-ray powder diffraction spectral peak(s) selected from the peaks listed in Table F below.

TABLE F

XRPD Peak Positions for Form J of Compound 1 Fumarate Salt

| Position (°2θ) | Intensity % |
|---|---|
| 4.9 | 7.7 |
| 10.0 | 11.2 |
| 11.5 | 100 |
| 12.3 | 49.7 |
| 14.9 | 99.7 |
| 15.6 | 92.1 |
| 16.5 | 5.8 |
| 18.6 | 23.9 |
| 20.1 | 19.4 |
| 21.2 | 18.0 |
| 22.6 | 25.2 |
| 22.8 | 13.5 |
| 25.4 | 5.9 |
| 26.5 | 7.3 |

In this and all subsequent tables, the position (°2θ) is within ± 0.2.

In some embodiments, Form J of Compound 1 fumarate salt is characterized in that it has one or more peaks in its X-ray powder diffraction pattern selected from those at about 11.5, about 14.9, and about 15.6 degrees 2-theta. In some embodiments, Form J of Compound 1 fumarate salt is characterized in that it has two or more peaks in its X-ray powder diffraction pattern selected from those at about 11.5, about 14.9, and about 15.6 degrees 2-theta. In some embodiments, Form J of Compound 1 fumarate salt is characterized in that it has three peaks in its X-ray powder diffraction pattern at about 11.5, about 14.9, and about 15.6 degrees 2-theta. In some embodiments, Form J of Compound 1 is characterized by a DSC thermogram having an endothermic event at about 228° C. In some embodiments, Form J of Compound 1 fumarate salt is characterized by a TGA curve showing minimal mass loss up to a temperature of about 147° C. and only about 2% mass loss at about 200° C., suggesting that Form J is an anhydrous, non-solvated form.

Form J can be isolated by the following procedure: Add about 6.5 g of Compound 1 free base and about 1010 mg of fumaric acid powder to a vessel. Add about 130 mL of isopropanol to the vessel and stir and head to vessel to 70° C. for 3 hours to obtain a suspension. Cool the suspension to room temperature over about 3 hours and continue to stir for about 18 hours. Filter the suspension to collect the solid Form J of Compound 1 fumarate salt.

In some embodiments, the microparticles of Compound 1 fumaric acid salt Form J are substantially pure. In some embodiments, the microparticles of Compound 1 comprise fumaric acid salt Form J and are substantially free of amorphous Compound 1 and other crystalline forms of Compound 1. In certain embodiments, the microparticles comprise at least about 95% by weight of crystalline Compound 1 fumaric acid salt Form J. In some embodiments of the disclosure, the microparticles comprise at least about 99% by weight of crystalline Compound 1 fumaric acid salt Form J.

In some embodiments, the microparticles of Compound 1 have a median particle size ($D_{50}$) of about 1.0 μm, about 1.1 μm, about 1.2 μm, about 1.3 μm, about 1.4 μm, about 1.5 μm, about 1.6 μm, about 1.7 μm, about 1.8 μm, about 1.9 μm, or about 2.0 μm. In some embodiments, the microparticles of Compound 1 have a median particle size ($D_{50}$) of about 1.0 μm to about 2.0 μm. In some embodiments, the microparticles of Compound 1 have a particle size distribution span ($[D_{90}-D_{10}]/D_{50}$) less than about 3, less than about 2.5, less than about 2, less than about 1.5, less than about 1, less than about 0.8, or less than about 0.5. In some embodiments, the microparticles of Compound 1 have a median particle size ($D_{50}$) of about 1.0 µm to about 2.0 µm and a span less than about 3.

In some embodiments, Compound 1 is present in the pharmaceutical composition in an amount from about 20 wt % to about 70 wt %. In some embodiments, Compound 1 is present in the pharmaceutical composition in an amount from about 30 wt % to about 60 wt %. In some embodiments, Compound 1 is present in the pharmaceutical composition in an amount from about 35 wt % to about 55 wt %. In some embodiments, Compound 1 is present in the pharmaceutical composition in an amount from about 40 wt % to about 50 wt %. In some embodiments, Compound 1 is present in the pharmaceutical composition in an amount of about 20 wt %, about 30 wt %, about 35 wt %, about 36 wt %, about 37 wt %, about 38 wt %, about 39 wt %, about 40 wt %, about 41 wt %, about 42 wt %, about 43 wt %, about 44 wt %, about 45 wt %, about 46 wt %, about 47 wt %, about 48 wt %, about 49 wt %, about 50 wt %, about 51 wt %, about 52 wt %, about 53 wt %, about 54 wt %, about 55 wt %, about 56 wt %, about 57 wt %, about 58 wt %, about 59 wt %, about 60 wt %, or about 70 wt %. In some embodiments, Compound 1 is present in the pharmaceutical composition in an amount of about 50 wt %.

In some embodiments, the pharmaceutical composition comprises microparticles of Compound 1 in the form of free base solid form $H^4$, wherein the microparticles have a median particle size of about 1.0 µm to about 2.0 µm, with a particle size distribution span less than about 3.0, and wherein Compound 1 is present in the pharmaceutical composition in an amount of about 50 wt %.

In some embodiments, the pharmaceutical composition comprises microparticles of Compound 1 in the form of HCl salt Form I, wherein the microparticles have a median particle size ($D_{50}$) of about 1.0 µm, about 1.1 µm, about 1.2 µm, about 1.3 µm, about 1.4 µm, about 1.5 µm, about 1.6 µm, about 1.7 µm, about 1.8 µm, about 1.9 µm, or about 2.0 µm. In some embodiments, the pharmaceutical composition comprises microparticles of Compound 1 in the form of HCl salt Form I, wherein the microparticles have a median particle size ($D_{50}$) of about 1.0 µm to about 2.0 µm. In some embodiments, the pharmaceutical composition comprises microparticles of Compound 1 in the form of HCl salt Form I, wherein the microparticles have a particle size distribution span less than about 3, less than about 2.5, less than about 2, less than about 1.5, less than about 1, less than about 0.8, or less than about 0.5. In some embodiments, the pharmaceutical composition comprises microparticles of Compound 1 in the form of HCl salt Form I, wherein the microparticles have a median particle size ($D_{50}$) of about 1.0 µm to about 2.0 µm and a span less than about 3.

In some embodiments, the pharmaceutical composition comprises microparticles of Compound 1 in the form of HCl salt Form I, wherein Compound 1 is present in the pharmaceutical composition in an amount from about 20 wt % to about 91 wt %, based on the amount of free base Compound 1 present in the composition. In some embodiments, the pharmaceutical composition comprises microparticles of Compound 1 in the form of HCl salt Form I, wherein Compound 1 is present in the pharmaceutical composition in an amount of about 20 wt %, about 30 wt %, about 35 wt %, about 40 wt %, about 45 wt %, about 46 wt %, about 47 wt %, about 48 wt %, about 49 wt %, about 50 wt %, about 55 wt %, about 60 wt %, about 65 wt %, about 70 wt %, about 75 wt %, about 80 wt %, about 85 wt %, or about 90 wt %, or any ranges or individual whole number wt % values therebetween, based on the amount of free base Compound 1 present in the composition.

In some embodiments, the pharmaceutical composition comprises microparticles of Compound 1 in the form of HCl salt Form I, further comprising one or more additional components described herein. In some embodiments, the pharmaceutical composition comprises microparticles of Compound 1 in the form of HCl salt Form I, and one or more of an acidulant, surfactant, a filler, a disintegrant, a lubricant, a glidant, a stabilizer, a coloring agent, a sweetener and a flavorant, or any combinations thereof.

B. Acidulant

As defined above, a pharmaceutical composition of the present invention is a micronized powder comprising an acidulant.

In some embodiments, the pharmaceutical composition comprises an acidulant selected from citric acid, ascorbic acid, tartaric acid, acetic acid, fumaric acid, lactic acid, and malic acid, or a salt of any of the aforementioned acids. In some embodiments, the pharmaceutical composition comprises an acidulant selected from citric acid, ascorbic acid, and tartaric acid, or a salt of any of the aforementioned acids. In some embodiments, the acidulant is citric acid, or a salt thereof. In some embodiments, the acidulant is citric acid. In some embodiments, the acidulant is anhydrous citric acid.

In some embodiments, the acidulant is any acidulant commonly utilized in the formulation of pharmaceutical compositions for oral administration.

In some embodiments, the acidulant is present in the pharmaceutical composition in an amount from about 5 wt % to about 55 wt %. In some embodiments, acidulant is present in the pharmaceutical composition in an amount from about 10 wt % to about 45 wt %. In some embodiments, acidulant is present in the pharmaceutical composition in an amount of about 5 wt %, about 6 wt %, about 7 wt %, about 8 wt %, about 9 wt %, about 10 wt %, about 10.5 wt %, about 11 wt %, about 12 wt %, about 12.5 wt %, about 13 wt %, about 14 wt %, about 15 wt %, about 16 wt %, about 17 wt %, about 18 wt %, about 19 wt %, about 20 wt %, about 21 wt %, about 22 wt %, about 23 wt %, about 24 wt %, about 25 wt %, about 26 wt %, about 27 wt %, about 28 wt %, about 29 wt %, about 30 wt %, about 31 wt %, about 32 wt %, about 33 wt %, about 34 wt %, about 35 wt %, about 36 wt %, about 37 wt %, about 38 wt %, about 39 wt %, about 40 wt %, about 41 wt %, about 42 wt %, about 43 wt %, about 44 wt %, about 45 wt %, about 46 wt %, about 47 wt %, about 48 wt %, about 49 wt %, about 50 wt %, about 51 wt %, about 52 wt %, about 53 wt %, about 54 wt %, or about 55 wt %. In some embodiments, acidulant is present in the pharmaceutical composition in an amount of about 10 wt %. In some embodiments, acidulant is present in the pharmaceutical composition in an amount of about 12.5 wt %. In some embodiments, acidulant is present in the pharmaceutical composition in an amount of about 15 wt %. In some embodiments, acidulant is present in the pharmaceutical composition in an amount of about 45 wt %. In some embodiments, acidulant is present in the pharmaceutical composition in an amount of about 50 wt %.

In some embodiments, the acidulant is citric acid, present in the pharmaceutical composition in an amount of about 45 wt %.

In some embodiments, the acidulant is citric acid, wherein the citric acid is in the form of microparticles. In some embodiments, the citric acid microparticles have a median particle size ($D_{50}$) of about 10 µm, about 20 µm, about 50 µm, about 75 µm, about 100 µm, about 150 µm, about 200

μm, about 250 μm, about 300 μm, about 350 μm, about 400 μm, about 450 μm, about 500 μm, about 550 μm, or about 600 μm, or any value or range therebetween. In some embodiments, the pharmaceutical composition comprises microparticles of citric acid wherein the microparticles have a median particle size ($D_{50}$) of about 100 μm to about 400 μm. In some embodiments, the pharmaceutical composition comprises microparticles of citric acid wherein the microparticles have a median particle size ($D_{50}$) of about 200 μm to about 300 μm. In some embodiments, the pharmaceutical composition comprises microparticles of citric acid wherein the microparticles have a median particle size ($D_{50}$) of about 250 μm.

C. Surfactant

As defined above, a pharmaceutical composition of the present invention is a micronized powder comprising a surfactant.

In some embodiments, the pharmaceutical composition comprises a surfactant selected from polyoxylethylene stearate, sorbitan stearate, sorbitan sesquioleate, sorbitan monooleate, Polysorbate 20, Polysorbate 80, sodium dodecyl sulfate (SDS; alternatively referred to as sodium lauryl sulfate, abbreviated as SLS), poloxamer 188 (KOLLIPHOR® P188), poloxamer 407 (KOLLIPHOR® P407 micro), Lauroyl polyoxyl-32 glycerides (GELUCIRE® 44/14), Glyceryl monooleate type 40 (Peceol™), d-α-Tocopheryl polyethylene glycol 1000 succinate (Vitamin E TPGS) and bis(2-ethylhexyl) sulfosuccinate, also known as dioctyl sulfosuccinate (DOSS). In some embodiments, the surfactant is polysorbate 80. In some embodiments, the surfactant is SDS. In some embodiments, the surfactant is a commercial product comprising SDS, such as STEPANOL® WA-100.

In some embodiments, the surfactant is any surfactant commonly utilized in the formulation of pharmaceutical compositions for oral administration.

In some embodiments, the surfactant is present in the pharmaceutical composition in an amount from about 1 wt % to about 20 wt %. In some embodiments, the surfactant is present in the pharmaceutical composition in an amount from about 5 wt % to about 15 wt %. In some embodiments, the surfactant is present in the pharmaceutical composition in an amount of about 1 wt %, 2 wt %, about 3 wt %, about 4 wt %, about 5 wt %, about 6 wt %, about 7 wt %, about 8 wt %, about 9 wt %, about 10 wt %, about 11 wt %, about 12 wt %, about 12.5 wt %, about 13 wt %, about 14 wt %, about 15 wt %, about 16 wt %, about 17 wt %, about 18 wt %, about 19 wt %, or about 20 wt %. In some embodiments, the stabilizer is present in the pharmaceutical composition in an amount of about 5 wt %.

In some embodiments, the pharmaceutical composition comprises a surfactant which is SDS in an amount of about 5 wt %.

D. Additional Ingredients

As defined above, a pharmaceutical composition of the present invention is a micronized powder optionally comprising one or more additional ingredients, selected from, but not necessarily limited to, a filler, a disintegrant, a lubricant, a glidant, a stabilizer, a coloring agent, a sweetener and a flavorant.

In some embodiments, the pharmaceutical composition optionally comprises one or more stabilizers. In some embodiments, the stabilizer comprises an organic polymer. In some embodiments, the stabilizer comprises an organic polymer comprising cellulose or a derivative thereof. In some embodiments, the stabilizer comprises hydroxylpropylcellulose (HPC) or hydroxypropyl methylcellulose (HPMC). In some embodiments, the stabilizer comprises an organic polymer. In some embodiments, the organic polymer comprises polypropylene oxide, polyethylene oxide or a combination thereof. In some embodiments, the stabilizer comprises an organic polymer comprising polyvinylpyrrolidone, or a derivative thereof. In some embodiments, the stabilizer comprises polyvinylpyrrolidone, or a polyvinylpyrrolidone copolymer. In some embodiments, the stabilizer comprises a vinylpyrollidone-vinyl acetate copolymer. In some embodiments, the stabilizer comprises hydroxypropyl methylcellulose acetate succinate.

In some embodiments, the stabilizer comprises one or more commercial stabilizers selected from EUDRAGIT EPO, PVP K-30 polymer (ASHLAND™), KOLLIDON® VA 64 (BASF®), Plasdone K-29/32 (ASHLAND™), KLUCELTMHPC (ASHLAND™), Hydroxypropyl methylcellulose acetate succinate (AQUASOLVE™ HPMC-AS MF) and HPMC PHARMACOAT®603.

In some embodiments, the stabilizer is any stabilizer commonly utilized in the formulation of pharmaceutical compositions for oral administration.

In some embodiments, the pharmaceutical composition optionally comprises one or more diluents, bulking agents or fillers. In some embodiments, the filler is selected from sorbitol, isomalt, mannitol, starch, cellulose, dibasic calcium phosphates dihydrate, lactose monohydrate, pregelatinized starch, or combinations thereof. In some embodiments the filler is microcrystalline cellulose.

In some embodiments, the pharmaceutical composition optionally comprises one or more disintegrants. In some embodiments, the disintegrant is selected from croscarmellose sodium type A (SoluTab), sodium starch glycolate type A (Glycolys), crospovidone (Polyplasdone XL 10) or combinations thereof.

In some embodiments, the pharmaceutical composition optionally comprises one or more lubricants. In some embodiments, the lubricant is magnesium stearate.

In some embodiments, the pharmaceutical composition optionally comprises one or more glidants. In some embodiments, the glidant is colloidal silicon dioxide.

In some embodiments, the pharmaceutical composition optionally comprises one or more sweeteners and flavorants to improve the palatability of the composition. In some embodiments, the pharmaceutical composition comprises a flavorant such as, but not limited to, a vanilla flavoring or a strawberry flavoring. In some embodiments, the pharmaceutical composition comprises a sweetener such as, but not limited to, sucralose, aspartame, sodium saccharin or calcium saccharin.

In some embodiments, the pharmaceutical composition optionally comprises one or more incidental additional ingredients. In some embodiments, the pharmaceutical composition comprises an incidental additional ingredient introduced to the pharmaceutical composition during the manufacturing process of the pharmaceutical composition. In some embodiments, the additional ingredient is a solvent. In some embodiments, the additional ingredient is isopropanol.

E. Formulation

As described above, in some embodiments, the pharmaceutical composition is a micronized blend comprising, or consisting essentially of:

(i) Compound 1;
(ii) an acidulant;
(iii) a surfactant; and optionally one or more of: a filler, a disintegrant, a lubricant, a glidant, a stabilizer, a coloring agent, a sweetener and a flavorant.

In some embodiments, the pharmaceutical composition comprises, or consists essentially of:
(i) Compound 1, or a pharmaceutically acceptable salt thereof;
(ii) an acidulant;
(iii) a surfactant; and
optionally one or more of: a filler, a disintegrant, a lubricant, a glidant, a stabilizer, a coloring agent, a sweetener and a flavorant.

In some embodiments, the pharmaceutical composition comprises, or consists essentially of:
(i) Compound 1 in an amount of about 35 wt % to about 55 wt %;
(ii) an acidulant in an amount of about 5 wt % to about 50 wt %;
(iii) a surfactant in an amount of about 1 wt % to about 20 wt %; and
optionally one or more of: a filler, a disintegrant, a lubricant, a glidant, a stabilizer, a coloring agent, a sweetener and a flavorant.

In some embodiments, the pharmaceutical composition comprises, or consists essentially of:
(i) Compound 1 in an amount of about 35 wt % to about 55 wt %;
(ii) an acidulant in an amount of about 5 wt % to about 50 wt %; and
(iii) a surfactant in an amount of about 1 wt % to about 20 wt %.

In some embodiments, the pharmaceutical composition comprises, or consists essentially of:
(i) Compound 1 in an amount of about 45 wt % to about 50 wt %;
(ii) an acidulant in an amount of about 10 wt % to about 45 wt %;
(iii) a surfactant in an amount of about 5 wt % to about 15 wt %.

In some embodiments, the pharmaceutical composition comprises, or consists essentially of:
(i) Compound 1 in an amount of about 50 wt %;
(ii) an acidulant in an amount of about 45 wt %; and
(iii) a surfactant in an amount of about 5 wt %.

In some embodiments, the pharmaceutical composition comprises, or consists essentially of:
(i) Compound 1 in the form of crystalline free base Form $H^A$;
(ii) citric acid;
(iii) SDS.

In some embodiments, the pharmaceutical composition comprises, or consists essentially of:
(i) Compound 1 in the form of crystalline free base Form $H^A$;
(ii) anhydrous citric acid; and
(iii) SDS.

In some embodiments, the pharmaceutical composition comprises, or consists essentially of:
(i) Compound 1 in the form of crystalline free base Form $H^A$ microparticles;
(ii) anhydrous citric acid; and
(iii) SDS.

In some embodiments, the pharmaceutical composition comprises, or consists essentially of:
(i) Compound 1 in the form of crystalline free base Form $H^A$ microparticles, in an amount of about 35 wt % to about 55 wt %;
(ii) anhydrous citric acid in an amount of about 5 wt % to about 50 wt %; and
(iii) SDS in an amount of about 1 wt % to about 20 wt %.

In some embodiments, the pharmaceutical composition comprises, or consists essentially of:
(i) Compound 1 in the form of crystalline free base Form $H_A$ microparticles, in an amount of about 45 wt % to about 50 wt %;
(ii) anhydrous citric acid in an amount of about 10 wt % to about 45 wt %; and
(iii) SDS in an amount of about 5 wt % to about 15 wt %.

In some embodiments, the pharmaceutical composition comprises, or consists essentially of:
(i) Compound 1 in the form of crystalline free base Form $H_A$ microparticles, in an amount of about 50 wt %;
(ii) anhydrous citric acid in an amount of about 45 wt %; and
(iii) SDS in an amount of about 5 wt %.

In some embodiments, the pharmaceutical composition comprises, or consists essentially of:
(i) Compound 1 in the form of crystalline free base Form $H^4$ microparticles having a median particle size of about 1.0 μm to about 2.0 μm, with a particle size distribution span less than about 3;
(ii) anhydrous citric acid; and
(iii) SDS.

In some embodiments, the pharmaceutical composition comprises, or consists essentially of:
(i) Compound 1 in the form of crystalline free base Form $H^4$ microparticles having a median particle size of about 1.0 μm to about 2.0 μm, with a particle size distribution span less than about 3, in an amount of about 35 wt % to about 55 wt %;
(ii) anhydrous citric acid in an amount of about 5 wt % to about 50 wt %; and
(iii) SDS in an amount of about 1 wt % to about 20 wt %.

In some embodiments, the pharmaceutical composition comprises, or consists essentially of:
(i) Compound 1 in the form of crystalline free base Form $H^4$ microparticles having a median particle size of about 1.0 μm to about 2.0 μm, with a particle size distribution span less than about 3, in an amount of about 45 wt % to about 50 wt %;
(ii) anhydrous citric acid in an amount of about 10 wt % to about 45 wt %; and
(iii) SDS in an amount of about 5 wt % to about 15 wt %.

In some embodiments, the pharmaceutical composition comprises, or consists essentially of:
(i) Compound 1 in the form of crystalline free base Form $H^4$ microparticles having a median particle size of about 1.0 μm to about 2.0 μm, with a particle size distribution span less than about 3, in an amount of about 50 wt %;
(ii) anhydrous citric acid in an amount of about 45 wt %; and
(iii) SDS in an amount of about 5 wt %.

In some embodiments, the pharmaceutical composition comprises, or consists essentially of:
(i) Compound 1, or a pharmaceutically acceptable salt thereof, in an amount of about 35 wt % to about 55 wt %;
(ii) an acidulant in an amount of about 5 wt % to about 50 wt %;
(iii) a surfactant in an amount of about 1 wt % to about 20 wt %; and
optionally one or more of: a filler, a disintegrant, a lubricant, a glidant, a stabilizer, a coloring agent, a sweetener and a flavorant.

In some embodiments, the pharmaceutical composition comprises, or consists essentially of:
(i) Compound 1, or a pharmaceutically acceptable salt thereof, in an amount of about 35 wt % to about 55 wt %;

(ii) an acidulant in an amount of about 5 wt % to about 50 wt %; and (iii) a surfactant in an amount of about 1 wt % to about 20 wt %.

In some embodiments, the pharmaceutical composition comprises, or consists essentially of:

(i) Compound 1, or a pharmaceutically acceptable salt thereof, in an amount of about 45 wt % to about 50 wt %;

(ii) an acidulant in an amount of about 10 wt % to about 45 wt %;

(iii) a surfactant in an amount of about 5 wt % to about 15 wt %.

In some embodiments, the pharmaceutical composition comprises, or consists essentially of:

(i) Compound 1, or a pharmaceutically acceptable salt thereof, in an amount of about 50 wt %;

(ii) an acidulant in an amount of about 45 wt %; and (iii) a surfactant in an amount of about 5 wt %.

In some embodiments, the pharmaceutical composition comprises, or consists essentially of:

(i) Compound 1 in the form of crystalline HCl salt Form I;

(ii) citric acid;

(iii) SDS.

In some embodiments, the pharmaceutical composition comprises, or consists essentially of:

(i) Compound 1 in the form of crystalline HCl salt Form I;

(ii) anhydrous citric acid; and (iii) SDS.

In some embodiments, the pharmaceutical composition comprises, or consists essentially of:

(i) Compound 1 in the form of crystalline HCl salt Form Imicroparticles;

(ii) anhydrous citric acid; and (iii) SDS.

In some embodiments, the pharmaceutical composition comprises, or consists essentially of:

(i) Compound 1 in the form of crystalline HCl salt Form Imicroparticles, in an amount of about 35 wt % to about 55 wt %;

(ii) anhydrous citric acid in an amount of about 5 wt % to about 50 wt %; and (iii) SDS in an amount of about 1 wt % to about 20 wt %.

In some embodiments, the pharmaceutical composition comprises, or consists essentially of:

(i) Compound 1 in the form of crystalline HCl salt Form Imicroparticles, in an amount of about 45 wt % to about 50 wt %;

(ii) anhydrous citric acid in an amount of about 10 wt % to about 45 wt %; and (iii) SDS in an amount of about 5 wt % to about 15 wt %.

In some embodiments, the pharmaceutical composition comprises, or consists essentially of:

(i) Compound 1 in the form of crystalline HCl salt Form Imicroparticles, in an amount of about 50 wt %;

(ii) anhydrous citric acid in an amount of about 45 wt %; and (iii) SDS in an amount of about 5 wt %.

In some embodiments, the pharmaceutical composition comprises, or consists essentially of:

(i) Compound 1 in the form of crystalline HCl salt Form I microparticles having a median particle size of about 1.0 µm to about 2.0 µm, with a particle size distribution span less than about 3;

(ii) anhydrous citric acid; and (iii) SDS.

In some embodiments, the pharmaceutical composition comprises, or consists essentially of:

(i) Compound 1 in the form of crystalline HCl salt Form I microparticles having a median particle size of about 1.0 µm to about 2.0 µm, with a particle size distribution span less than about 3, in an amount of about 35 wt % to about 55 wt %;

(ii) anhydrous citric acid in an amount of about 5 wt % to about 50 wt %; and (iii) SDS in an amount of about 1 wt % to about 20 wt %.

In some embodiments, the pharmaceutical composition comprises, or consists essentially of:

(i) Compound 1 in the form of crystalline HCl salt Form I microparticles having a median particle size of about 1.0 µm to about 2.0 µm, with a particle size distribution span less than about 3, in an amount of about 45 wt % to about 50 wt %;

(ii) anhydrous citric acid in an amount of about 10 wt % to about 45 wt %; and (iii) SDS in an amount of about 5 wt % to about 15 wt %.

In some embodiments, the pharmaceutical composition comprises, or consists essentially of:

(i) Compound 1 in the form of crystalline HCl salt Form I microparticles having a median particle size of about 1.0 µm to about 2.0 µm, with a particle size distribution span less than about 3, in an amount of about 50 wt %;

(ii) anhydrous citric acid in an amount of about 45 wt %; and (iii) SDS in an amount of about 5 wt %.

In some embodiments, any of the pharmaceutical compositions described above optionally further comprise one or more of: a filler, a disintegrant, a lubricant, a glidant, a stabilizer, a coloring agent, a sweetener and a flavorant.

In some embodiments, the pharmaceutical composition further comprises a capsule containing a micronized powder of the present disclosure. In some embodiments, the capsule is appropriate for oral administration. In some embodiments, the capsule shell comprises gelatin. In some embodiments, the capsule comprises hydroxypropyl methylcellulose (HPMC).

In some embodiments, a pharmaceutical composition of the present disclosure is pressed into a tablet formulated for oral administration.

Uses of Compounds and Pharmaceutically Acceptable Compositions

As described generally above, Compound 1, and pharmaceutically acceptable solid compositions thereof described herein, are inhibitors of c-kit kinase. The c-kit kinase inhibiting compounds of the present disclosure can, in some embodiments, find use in inhibiting activity of a target c-kit kinase in vitro or in vivo. Aspects of the subject methods include contacting a sample comprising an effective amount of a c-kit kinase inhibiting compound (e.g., as described herein) to determine whether the desired activity exists.

In one aspect, the present disclosure provides methods for treating a c-kit kinase mediated disease or disorder in a subject in need thereof. In some embodiments, the method comprises administering to the subject in need thereof a therapeutically effective amount of a pharmaceutical composition disclosed herein, i.e., a pharmaceutical composition comprising Compound 1. In some embodiments, the disease or disorder is a mast-cell associated disease, a respiratory disease, an inflammatory disorder, an autoimmune disorder, a metabolic disease, a fibrosis disease, or a dermatological disease. In some embodiments, the disease or disorder is asthma, allergic rhinitis, pulmonary arterial hypertension (PAH), primary pulmonary hypertension (PPH), pulmonary fibrosis, hepatic fibrosis, cardiac fibrosis, scleroderma, irritable bowel syndrome (IBS), inflammatory bowel disease (IBD), urticaria, dermatosis, atopic dermatitis, allergic contact dermatitis, rheumatoid arthritis, multiple sclerosis, melanoma, a gastrointestinal stromal tumor, a mast cell tumor, mastocytosis, anaphylactic syndrome, food allergy, type I diabetes or type II diabetes. In some embodiments, the administration is oral administration.

In another aspect, the present disclosure provides a pharmaceutical composition as disclosed herein, i.e., a pharmaceutical composition comprising Compound 1, for use in treating a c-kit kinase mediated disease or disorder in a subject in need thereof. In yet another aspect, the present disclosure provides a pharmaceutical composition as disclosed herein, i.e., a pharmaceutical composition comprising Compound 1, for the manufacture of a medicament for treating a c-kit kinase mediated disease or disorder in a subject in need thereof. In some embodiments, the disease or disorder is a mast-cell associated disease, a respiratory disease, an inflammatory disorder, an autoimmune disorder, a metabolic disease, a fibrosis disease, or a dermatological disease. In some embodiments, the disease or disorder is asthma, allergic rhinitis, pulmonary arterial hypertension (PAH), primary pulmonary hypertension (PPH), pulmonary fibrosis, hepatic fibrosis, cardiac fibrosis, scleroderma, irritable bowel syndrome (IBS), inflammatory bowel disease (IBD), urticaria, dermatosis, atopic dermatitis, allergic contact dermatitis, rheumatoid arthritis, multiple sclerosis, melanoma, a gastrointestinal stromal tumor, a mast cell tumor, mastocytosis, anaphylactic syndrome, food allergy, type I diabetes or type II diabetes.

As used herein, the terms "combination," "combined," and related terms refer to the simultaneous or sequential administration of therapeutic agents in accordance with this disclosure. For example, a described pharmaceutical composition may be administered with another therapeutic agent simultaneously or sequentially in separate unit dosage forms or together in a single unit dosage form.

When the pharmaceutical compositions of this disclosure are administered in combination therapies with other agents, they may be administered sequentially or concurrently to the patient. Alternatively, pharmaceutical or prophylactic compositions according to this disclosure comprise a combination of Compound 1 and another therapeutic or prophylactic agent. Additional therapeutic agents that are normally administered to treat a particular disease or condition may be referred to as "agents appropriate for the disease, or condition, being treated."

In some embodiments, the subject method includes administering a therapeutically effective amount of one or more additional active agents. By combination therapy is meant that a c-kit inhibiting pharmaceutical composition can be used in a combination with another therapeutic agent to treat a single disease or condition. In particular embodiments, a pharmaceutical composition of the present disclosure is administered concurrently with the administration of another therapeutic agent.

The subject pharmaceutical composition can be administered in combination with other therapeutic agents in a variety of therapeutic applications. Therapeutic applications of interest for combination therapy include those applications in which activity of a target c-kit kinase is the cause or a compounding factor in disease progression. As such, the subject pharmaceutical composition find use in combination therapies in which the inhibition of a target c-kit kinase in the subject is desired.

The term "treatment" is used interchangeably herein with the term "therapeutic method" and refers to both 1) therapeutic treatments or measures that cure, slow down, lessen symptoms of, and/or halt progression of a diagnosed pathologic conditions, disease or disorder, and 2) and prophylactic/preventative measures. Those in need of treatment may include individuals already having a particular medical disease or disorder as well as those who may ultimately acquire the disorder (i.e., those at risk or needing preventive measures).

The term "subject" as used herein refers to any individual or patient to which the subject methods are performed. Generally, the subject is human, although as will be appreciated by those in the art, the subject may be an animal.

The terms "therapeutically effective amount", "effective dose", "therapeutically effective dose", "effective amount," or the like refer to the amount of a subject compound that will elicit the biological or medical response in a tissue, system, animal or human that is being sought by administering said compound. Generally, the response is either amelioration of symptoms in a patient or a desired biological outcome. In some embodiments, such amount should be sufficient to inhibit a c-kit kinase.

In some embodiments, an effective amount of a c-kit inhibiting compound for use in the invention is an amount that ranges from about 10 pg to 1000 mg, e.g., from about 10 pg to 50 pg, from about 50 pg to 150 pg, from about 150 pg to 250 pg, from about 250 pg to 500 pg, from about 500 pg to 750 pg, from about 750 pg to 1 ng, from about 1 ng to 10 ng, from about 10 ng to 50 ng, from about 50 ng to 150 ng, from about 150 ng to 250 ng, from about 250 ng to 500 ng, from about 500 ng to 750 ng, from about 750 ng to 1 mg, from about 1 pg to 10 pg, from about 10 pg to 50 pg, from about 50 pg to 150 pg, from about 150 pg to 250 pg, from about 250 pg to 500 pg, from about 500 pg to 750 pg, from about 750 pg to 1 mg, from about 1 mg to 50 mg, from about 1 mg to 100 mg, from about 50 mg to 100 mg, from about 100 mg to 200 mg, from about 200 mg to 300 mg, from about 300 mg to 400 mg, from about 400 mg to 500 mg, from about 100 mg to 500 mg, from about 500 mg to 1000 mg, or from about 100 mg to about 1000 mg. The amount can be a single dose amount or can be a total daily amount. The total daily amount can range from about 10 pg to 100 mg, or can range from about 100 mg to 500 mg, or can range from about 500 mg to 1000 mg. In some embodiments, an effective amount of a c-kit inhibiting compound for use in the invention is about 300 mg. In some embodiments, an effective amount of a c-kit inhibiting compound for use in the invention is about 500 mg. In some embodiments, an effective amount of a c-kit inhibiting compound for use in the invention is about 1 g.

Definitions

As used herein, the term "about", when used in reference to an amount refers to the stated value ±10% of said value. In some embodiments, "about" refers to the stated value ±5% of said value, ±2% of said value, or ±1% of said value.

As used herein, the terms "administer," "administering," and "administration," refer to any method which, in sound medical practice, delivers a provided composition, or an active agent contained therein, to a subject in such a manner as to provide a therapeutic effect.

As used herein, the phrases an "effective amount" or a "therapeutically effective amount" of an active agent or ingredient, or pharmaceutically active agent or ingredient, refer to an amount of the pharmaceutically active agent sufficient enough to have a therapeutic effect upon administration. Effective amounts of the pharmaceutically active agent will vary with the kind of pharmaceutically active agent chosen, the particular condition or conditions being treated, the severity of the condition, the duration of the treatment, the specific components of the composition being used, and like factors. Generally, the response is either amelioration of symptoms in a patient or a desired biological outcome. In some embodiments, such amount should be sufficient to inhibit a c-kit kinase and treat a c-kit kinase related disease or disorder.

As used herein, the term "microparticle" refers to a particle with a largest cross-sectional dimension of about 0.1 m to about 1000 m. The term "microparticle" also describes compositions of the present disclosure that may contain individual particles that fall outside of this range, wherein the average (mean) particle size of the particles in the composition falls within the range of about 0.1 m to about 1000 m.

As used herein, the phrase "pharmaceutically acceptable salts" refers to salts of certain ingredient(s) which possess the same activity as the unmodified compound(s) and which are neither biologically nor otherwise undesirable. A salt can be formed with, for example, organic or inorganic acids. Such suitable acids include acetic acid, acetylsalicylic acid, adipic acid, alginic acid, ascorbic acid, aspartic acid, benzoic acid, benzenesulfonic acid, bisulfic acid, boric acid, butyric acid, camphoric acid, camphorsulfonic acid, carbonic acid, citric acid, cyclopentanepropionic acid, digluconic acid, dodecylsulfic acid, ethanesulfonic acid, formic acid, fumaric acid, glyceric acid, glycerophosphoric acid, glycine, glucoheptanoic acid, gluconic acid, glutamic acid, glutaric acid, glycolic acid, hemisulfic acid, heptanoic acid, hexanoic acid, hippuric acid, hydrobromic acid, hydrochloric acid, hydroiodic acid, hydroxyethanesulfonic acid, lactic acid, maleic acid, malic acid, malonic acid, mandelic acid, methanesulfonic acid, mucic acid, naphthylanesulfonic acid, naphthylic acid, nicotinic acid, nitrous acid, oxalic acid, pelargonic, phosphoric acid, propionic acid, saccharin, salicylic acid, sorbic acid, succinic acid, sulfuric acid, tartaric acid, thiocyanic acid, thioglycolic acid, thiosulfuric acid, tosylic acid, undecylenic acid, and naturally and synthetically derived amino acids.

As used herein the term "preservative" refers to any known pharmaceutically acceptable preservative that functions by inhibiting bacteria, fungi, yeast, mold, other microbe, and/or by inhibiting oxidation. Suitable preservatives include but are not limited to antimicrobial agents and/or antioxidants. Suitable antimicrobial agents can include but are not limited to benzoates, benzyl alcohol, sodium benzoate, sorbates, propionates, and nitrites. Suitable antioxidants can include but are not limited to vitamin C, butylated hydroxytoluene (BHT), sulphites, and vitamin E. Other such preservatives for use in the present invention are described above and herein.

The term "prevent," "preventing," or "prevention," as used herein refers to any reduction, no matter how slight, of a subject's predisposition or risk for developing a condition, disease, disorder or symptom thereof. For purposes of prevention, the subject is any subject, and preferably is a subject that is at risk for, or is predisposed to, developing a condition, disease, disorder. The term "prevention" includes either preventing the onset of a clinically evident condition, disease, disorder altogether or preventing the onset of a pre-clinically evident condition, disease, disorder in individuals at risk. This includes prophylactic treatment of subjects at risk of developing condition, disease, disorder.

As used herein, the term "solvent" refers to any pharmaceutically acceptable medium which is a liquid at ambient temperature, in which one or more solutes can be dissolved, or one or more substances can be partially dissolved or suspended. Numerous solvents are well known in the chemical and pharmaceutical arts and are contemplated herein and below.

The phrase "substantially pure" as used herein refers to an individual compound form, which is substantially devoid of all other forms, as well as degradation products of a form, and any residual solvent, and is at least 85% pure on a % weight basis, unless otherwise specified. The compound form can have at least 90% purity on a % weight basis, at least 93% purity on a % weight basis, at least 95% purity on a % weight basis, or at least 97%, 98%, 99%, or 99.5% purity on a % weight basis.

As used herein, "subject" or "individual" or "animal" or "patient" or "mammal," refers to any subject, particularly a mammalian subject, for whom diagnosis, prognosis, or therapy is desired, for example, a human.

As used herein, a "treatment" or "treating" of a disease, disorder, or condition encompasses alleviation of at least one symptom thereof, a reduction in the severity thereof, or the delay or inhibition of the progression thereof. Treatment need not mean that the disease, disorder, or condition is totally cured. A useful composition herein needs only to reduce the severity of a disease, disorder, or condition, reduce the severity of symptoms associated therewith, provide improvement to a patient or subject's quality of life, or delay or inhibit the onset of a disease, disorder, or condition.

As used herein, all percentages are by weight of the total composition (i.e., wt %), unless otherwise specified.

Any concentration ranges, percentage range, or ratio range recited herein are to be understood as expressly disclosing and including any concentrations, percentages or ratios of any integer within that range and fractions thereof, such as one tenth and one hundredth of an integer, and any sub-range falling within a range, unless otherwise indicated.

Any number range recited herein relating to any physical feature, including for example, polymer subunits, size or thickness, are to be understood as expressly disclosing and including any integer or fraction of an integer within a disclosed range, or any sub-range within a disclosed range, unless otherwise indicated.

For the purpose of clarity, any element or feature of any method or composition or process described herein, can be combined with any other element or feature of any other method or composition or process described herein.

Other terms as used herein are meant to be defined by their well-known meanings in the art.

All features of each of the aspects of the disclosure apply to all other aspects mutatis mutandis. Each of the references referred to herein, including but not limited to patents, patent applications and journal articles, is incorporated by reference herein as though fully set forth in its entirety, In order that the disclosure described herein may be more fully understood, the following examples are set forth. It should be understood that these examples are for illustrative purposes only and are not to be construed as limiting this disclosure in any manner.

EXAMPLES

As depicted in the Examples below, in certain exemplary embodiments, compounds and compositions are prepared according to the following general procedures. The following examples are illustrative of the present pharmaceutical compositions and are not intended to be limitations thereon.
Materials and Methods Preparation of Free Base Forms a, $H^A$, $H^B$, and D, HCl Salt Form I and Fumaric Acid Salt Form J of Compound 1

Compound 1

Form A of Compound 1

Form A of compound 1 was prepared as disclosed in PCT/CN2020/090060, which is incorporated by reference herein:

Procedure A: About 2.0 g of amorphous Compound 1 (as prepared in Example F110 of WO 2013/033070 A1) was dissolved in 40 mL of IPA at 70° C. and mechanically stirred for 3 hours, resulting in a clear solution. The solution was then cooled to rt and continually stirred overnight. Precipitate formed overnight and was filtered and washed with IPA and dried overnight at 60° C. under vacuum. Characterization of the resulting material demonstrated crystalline Form A of Compound 1 free base.

Form $H^A$ of Compound 1

Form $H^A$ of Compound 1 was prepared as disclosed in PCT/CN2020/090060, which is incorporated by reference herein:

Procedure A: About 200 mg of Form A of Compound 1 was dissolved in 3.0 mL of MeOH/H$_2$O (1:1, v/v) and stirred at 1000 rpm at RT for 5 days. The suspension was centrifuged and the solids were dried under vacuum. Characterization of the resulting material demonstrated crystalline Form $H^A$ of Compound 1 free base.

Form $H^B$ of Compound 1

Form $H^B$ of Compound 1 was prepared as disclosed in PCT/CN2020/090060, which is incorporated by reference herein:

Procedure A: About 10 mg of Form A of Compound 1 was placed in a vial containing water for 2 weeks. The solid was isolated from the suspension and it was observed that Form A had been converted to Form $H^B$. Characterization of the resulting material demonstrated crystalline Form $H^B$ of Compound 1 free base.

Form D of Compound 1

Form D of compound 1 was prepared as follows:

Procedure A: 50° C. Slurry Screen—About 20 mg of Form A of Compound 1 was suspended in 0.5 mL of IPA in an HPLC vial. The sample was stirred magnetically (~1000 rpm) for about 7 days at 50° C., the remaining solids were isolated for XRPD analysis.

Procedure B: 50° C. Slurry Screen—About 20 mg of Form A of Compound 1 was suspended in 0.5 mL of CPME in an HPLC vial. The sample was stirred magnetically (~1000 rpm) for about 7 days at 50° C., the remaining solids were isolated for XRPD analysis.

Procedure C: Anti-solvent addition screen—About 20 mg of Form A of Compound 1 was dissolved in DCM to obtain a clear solution and the solution was magnetically stirred (~1000 rpm) followed by addition of MTBE until precipitate appeared. The obtained precipitate was isolated for XRPD analysis.

Procedure D: Anti-solvent addition screen—About 20 mg of Form A of Compound 1 was dissolved in pyridine to obtain a clear solution and the solution was magnetically stirred (~1000 rpm) followed by addition of EtOAc until precipitate appeared. The obtained precipitate was isolated for XRPD analysis.

Procedure E: 204.5 mg of Form A of Compound 1 was suspended in 3.0 mL IPA and stirred at 1000 rpm at RT for 5 days. The suspension was centrifuged and the solids were dried under vacuum. Characterization of the resulting material demonstrated crystalline Form D of Compound 1 free base.

Form I of Compound 1

Procedure A: 2008.0 mg of Compound 1 free base was added to a 100-mL bottle, followed by addition of 20 mL of isopropanol to obtain a suspension. 549.3 mg of HCl (36 wt % solution) was added to a 20 mL vial, followed by addition of 20 mL of isopropanol to obtain an HCl solution. The HCl solution was added to the 100-mL bottle and the mixture was stirred (500 rpm) at room temperature for 3 days. The mixture was filtered and the collected solids were dried under vacuum at room temperature overnight. The obtained precipitate was submitted for XRPD analysis.

Form J of Compound 1

Form J of Compound 1 was prepared substantially as disclosed in PCT/CN2020/090060, which is incorporated by reference herein:

Procedure A: 6.5 g of Compound 1 and 1009.775 mg of fumaric acid were mixed in a reactor. 130 ml of isopropanol was added to the mixture under mechanical stirring. The system was heated at 70° C. for 3 hours under stirring. The suspension was cooled to room temperature over 3 hours and continually stirred for 18 additional hours. The suspension was filtered by funnel and the wet cake was washed with isopropanol and dried at 30° C. under vacuum for 16 hours and at 60° C. under vacuum for 22 hours. The obtained solids were characterized by XRPD, DSC, TGA, NMR and HPLC (purity). The resulting material was determined to be 99.01% pure by HPLC. NMR analysis showed that the ratio of Compound 1: fumaric acid was 1:0.5.

Characterization Methods

PLM

Polarized light microscopy (PLM) was conducted using a Nikon LV100POL equipped with a 5 megapixel CCD and either a 20× and 50× physical lens.

XRPD

X-ray powder diffraction (XRPD) analysis was conducted using a Bruker D8 Advance diffractometer with the following parameters:

Tube: Cu: K-Alpha ($\lambda$=1.54060Å).
Generator: Voltage: 40 kV; Current: 40 mA;
Scan Scope: 3 to 40 deg, or 2 to 40 deg;
Scanning rate: 10 deg./min, or 19 deg./min;
Sample rotation speed: 15 rpm PSD for Powder Analysis About 50 mg of sample was placed into the tray and tested by PSD using the following parameters. Two parallel tests were run.

| | |
|---|---|
| Lens | R3 or R1 |
| Measuring Range | 0.5/0.9 μm < R3 < 175 μm |
| Trigger Conditions | Background test: 10 s<br>Time base: 10 ms<br>Trigger Conditions: fast test<br>Start: c.opt >= 1%<br>Valid: 2% <= c.opt <= 30%<br>Stop: is c.opt <= 2% or 2 s real time<br>Trigger termination: 60 s |
| Dispersing System | RODOS-OASISDRY<br>Injector: 4 mm<br>Dispersing medium: air<br>Dispersing method: 0.5 or 3.0 bar 65%<br>1.5 mm OASISDRY, feed rate = 65.00% |

UPLC

Ultra-performance liquid chromatography (UPLC) was used to measure the purity of the Compound 1 in certain samples. The following parameters were used:

| | | | |
|---|---|---|---|
| Instrument | Agilent 1290 infinityII | | |
| Column | ACQUITY UPLC BEH C18, 1.7 um 2.1*50 mm (PDS-HPLC-286) | | |
| | Time (min) | A %: 10 mM aq. NH$_4$OAC | B %: ACN |
| Gradient | 0 | 90 | 10 |
| | 4.0 | 45 | 55 |
| | 5.2 | 0 | 100 |
| | 5.21 | 90 | 10 |
| | 6.0 | 90 | 10 |
| Injection volume | 1 μL | | |
| Flow rate | 0.5 mL/min | | |

| | |
|---|---|
| Column Temp. | 30° C. |
| Wavelength | 240 nm |
| Diluent | ACN:H$_2$O = 7:3 |

HPLC

High performance liquid chromatography (HPLC) was used to measure the purity of the Compound 1 in certain samples. The following parameters were used:

| | | | |
|---|---|---|---|
| Instrument | Agilent 1260 infinityII | | |
| Column | XBridge C18, 3.5 um 3.0*150 mm (PDS-HPLC-367) | | |
| | Time (min) | A %: 10 mM aq. NH$_4$OAC | B %: ACN |
| Gradient | 0 | 80 | 20 |
| | 18 | 5 | 95 |
| | 21 | 5 | 95 |
| | 21.1 | 80 | 20 |
| | 27 | 80 | 20 |
| Injection volume | 2 μL | | |
| Flow rate | 0.8 mL/min | | |
| Column Temp. | 30° C. | | |
| Wavelength | 248 nm | | |
| Diluent | ACN:H$_2$O = 1:1 | | |

Materials

Sodium dodecyl sulfate (SDS) 99.0% was purchased from SIGMA. PVP-VA64 was purchased from BASF.

Micronization Equipment

Jetmill grinding was carried out using an Alpine Spiral Jet Mill 50 AS (HOSOKAWA MICRON).

Powder mixing was carried out using a Turbula T2F 2 liter powder mixer-shaker (TURBULA®).

Example 1: Micronization of Compound 1 Form H$^A$

Sample Preparation and Characterization

Compound 1 Form H$^A$ (10 g) was added stepwise to the injector of a jetmill grinding system and micronized at a gas pressure setting of 3-4 bar in 1 hour. The micronization process was repeated twice and the collected samples of micronized Compound 1 were analyzed. PLM imagery and XRPD (FIG. 1A) analysis showed that micronized Compound 1 remained crystalline and retained the same XRPD pattern as the Form H$^A$ starting material. The particle size distribution results showed $D_{10}$=0.59 μm, $D_{50}$=1.86 μm, and $D_{90}$=4.62 μm. By HPLC analysis, the micronized powder was found to be 98.88% pure, which was nearly identical to the starting material.

TABLE 1A

Characterization of micronized Compound 1 Form H$^A$ prepared by jetmill

| Formula No. | Yield | Appearance | PSD $D_{10}$ (μm) | PSD $D_{50}$ (μm) | PSD $D_{90}$ (μm) | XRPD | PLM | HPLC test Purity (%) |
|---|---|---|---|---|---|---|---|---|
| 1A | 47.1% | Pale grey powder, electrostatic, agglomerated | 0.59 | 1.86 | 4.62 | No form change | Birefringence | 98.88 |

1-Week and 4-Week Stability Studies of Formulation 1A

Figure 1B:
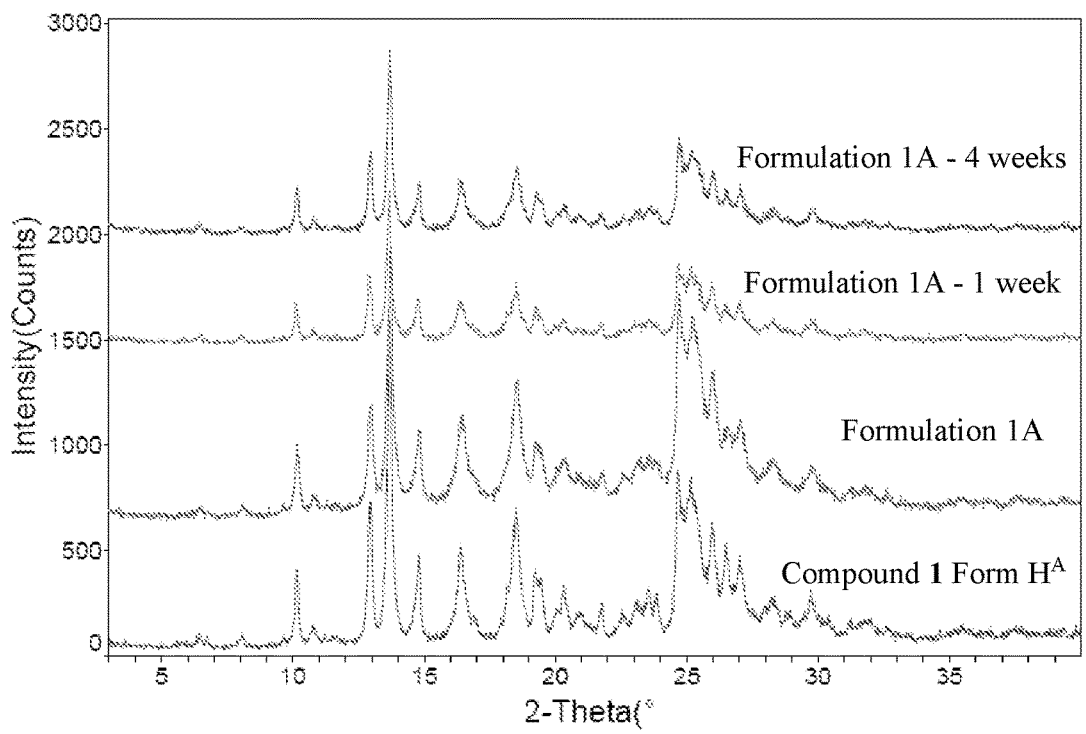
FIG. 1B depicts XRPD patterns for Formulation 1A after 1 week and 4 weeks stored at 25° C. and 60% relative humidity, as compared to Formula 1A before the stability study and Compound 1 Form $H^A$ starting material.

The chemical and physical stability of the micronized Formulation 1A was studied by placing the material in a 40-mL glass vial, covered by aluminum foil with pinholes and stored open under 25° C./60% RH for 1 week and 4 weeks. The 1-week and 4-week stability study results for Formulation 1A are reported below in Table 1B. XRPD spectra comparing the starting material and the micronized material after the 1 week and 4 week studies are shown in FIG. 1B.

PLM and XRPD patterns for Formulation 1A stored under 25° C./60% RH (open) for 1 week and 4 weeks both showed that the Compound 1 material remained crystalline with the same pattern as starting material. The particle size distribution results showed comparable $D_{50}$ after 1 week and 4 weeks as the initial sample. The purity HPLC results showed very little change, indicating that the micronized powder was chemically stable.

TABLE 1B 1 week and 4 week stability data of Formulation 1A

| Condition | Appearance | D$_{10}$ (μm) | | D$_{50}$ (μm) | | D$_{90}$ (μm) | | XRPD | PLM | HPLC test Purity (%) |
|---|---|---|---|---|---|---|---|---|---|---|
| Initial | Pale grey powder, electrostatic, agglomerated | | 0.59 | | 1.86 | | 4.62 | No form change | Birefringence | 98.88 |
| 25° C./60% RH, open, 1 W | Pale grey powder, electrostatic, agglomerated | 1<br>2<br>3<br>Avg | 0.62<br>0.62<br>0.62<br>0.62 | 1<br>2<br>3<br>Avg | 2.28<br>2.39<br>2.30<br>2.32 | 1<br>2<br>3<br>Avg | 5.59<br>5.74<br>5.65<br>5.66 | No form change | Birefringence | 98.75 |
| 25° C./60% RH, open, 4 W | Pale grey powder, electrostatic, agglomerated | 1<br>2<br>Avg | 0.59<br>0.58<br>0.59 | 1<br>2<br>Avg | 1.67<br>1.62<br>1.65 | 1<br>2<br>Avg | 4.40<br>4.38<br>4.39 | No form change | Birefringence | 98.75 |

Larger Scale Preparation and Characterization

Figure 1C:
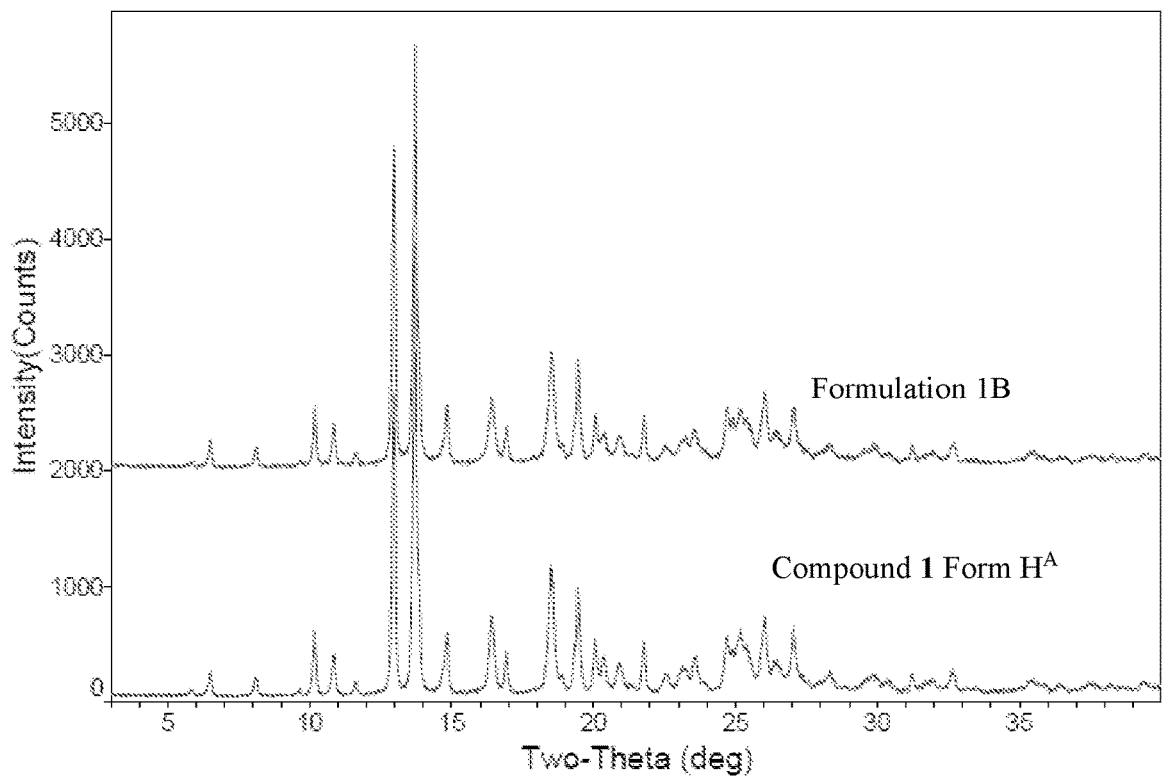
FIG. 1C depicts XRPD patterns for Formulation 1B, as compared to Compound 1 Form $H^A$ starting material.

Compound 1 Form H$^4$ (275 g) was added stepwise to the injector of a jetmill grinding system and micronized at a gas pressure setting of 3-4 bar with a feeding speed of about 10 g/hour. The collected samples of micronized Compound 1 were analyzed. PLM imagery and XRPD (FIG. 1C) analysis showed that micronized Compound 1 remained crystalline and retained the same XRPD pattern as the Form H$^4$ starting material. The particle size distribution results showed D$_{10}$=0.56 μm, D$_{50}$=1.45 μm, and D$_{90}$=4.93 m (pre- and post-grinding particle sizes shown in Table 1C). By HPLC analysis, the micronized powder was found to be 99.51% pure, which was identical to the starting material.

TABLE 1C

Characterization of larger scale micronized Compound 1 Form H$^4$ prepared by jetmill

| Formula No. | Appearance | D$_{10}$ (μm) | D$_{50}$ (μm) | D$_{90}$ (μm) | XRPD | PLM | HPLC test Purity (%) |
|---|---|---|---|---|---|---|---|
| 1B | Off-white powder, electrostatic, agglomerated | 1.10*<br>0.59# | 10.47*<br>1.86# | 35.11*<br>4.62# | No form change | Birefringence | 99.51 |

*Particle size before jetmill grinding;
Particle size after jetmill grinding

10-Day and 4-Week Stability Studies of Formulation 1B

Figure 1D:
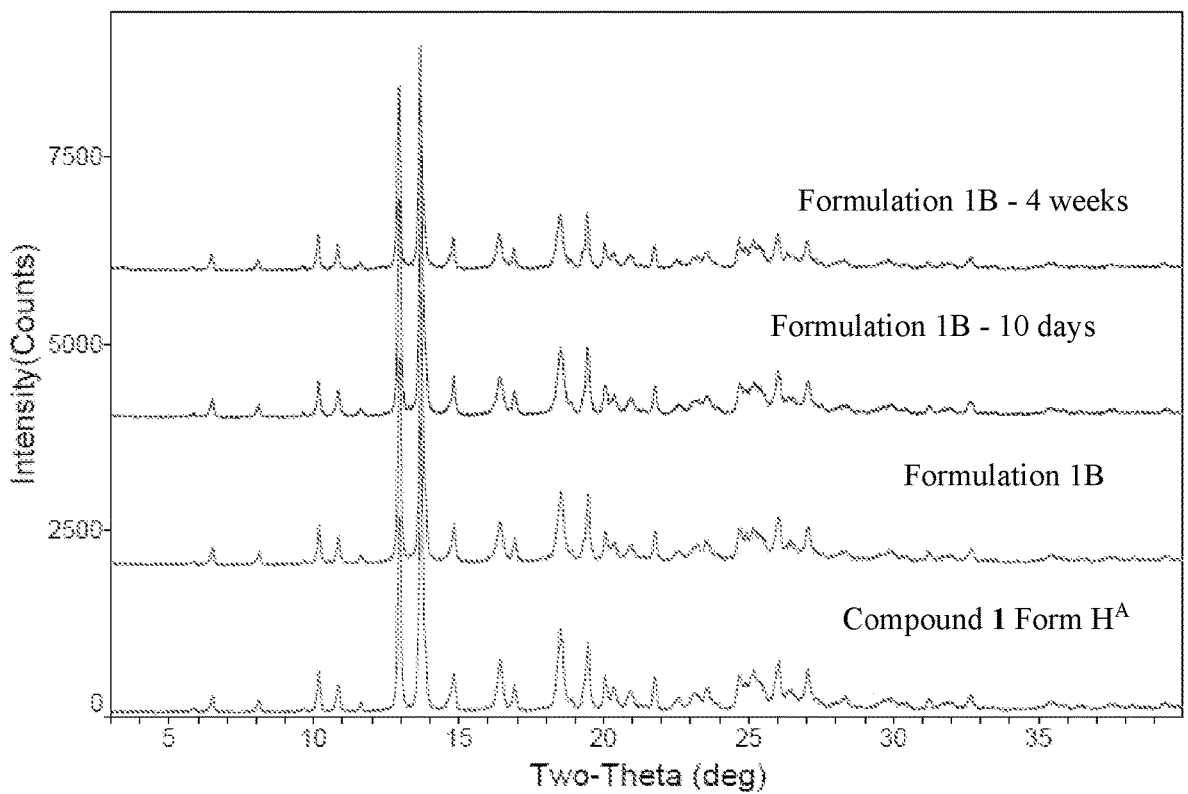
FIG. 1D depicts XRPD patterns for Formulation 1B after 10 days and 4 weeks stored at 25° C. and 60% relative humidity, as compared to Formula 1B before the stability study and Compound 1 Form $H^A$ starting material.

The chemical and physical stability of the micronized Formulation 1B was studied by placing the material in a 40-mL glass vial, covered by aluminum foil with pinholes and stored open under 25° C./60% RH for 10 days and 4 weeks. The 10-day and 4-week stability study results for Formulation 1B are reported below in Table 1D. XRPD spectra comparing the starting material and the micronized material after the 10 day and 4 week studies are shown in FIG. 1D.

PLM and XRPD patterns for Formulation 1B stored under 25° C./60% RH (open) for 10 days and 4 weeks both showed that the Compound 1 material remained crystalline with the same pattern as the unmilled starting material. The particle size distribution results showed comparable D$_{50}$ after 10 days and 4 weeks as the initial sample. The purity PLC results showed very little change, indicating that the micronized powder was chemically stable.

TABLE 1D 1 week and 4 week stability data of Formulation 1B

| Condition | Appearance | PSD | | | XRPD | PLM | HPLC test Purity (%) |
| --- | --- | --- | --- | --- | --- | --- | --- |
| | | $D_{10}$ (μm) | $D_{50}$ (μm) | $D_{90}$ (μm) | | | |
| initial | Off-white powder, electrostatic, agglomerated | 0.56 | 1.45 | 4.39 | No form change | Birefringence | 99.51 |
| 25° C./60% RH, open, 10 days | Off-white powder, electrostatic, agglomerated | 0.58 | 1.42 | 4.20 | No form change | Birefringence | 99.52 |
| 25° C./60% RH, open, 4 W | Off-white powder, electrostatic, agglomerated | 0.59 | 1.59 | 5.20 | No form change | Birefringence | 99.50 |

Further Larger Scale Preparation and Characterization

Figure 1E:
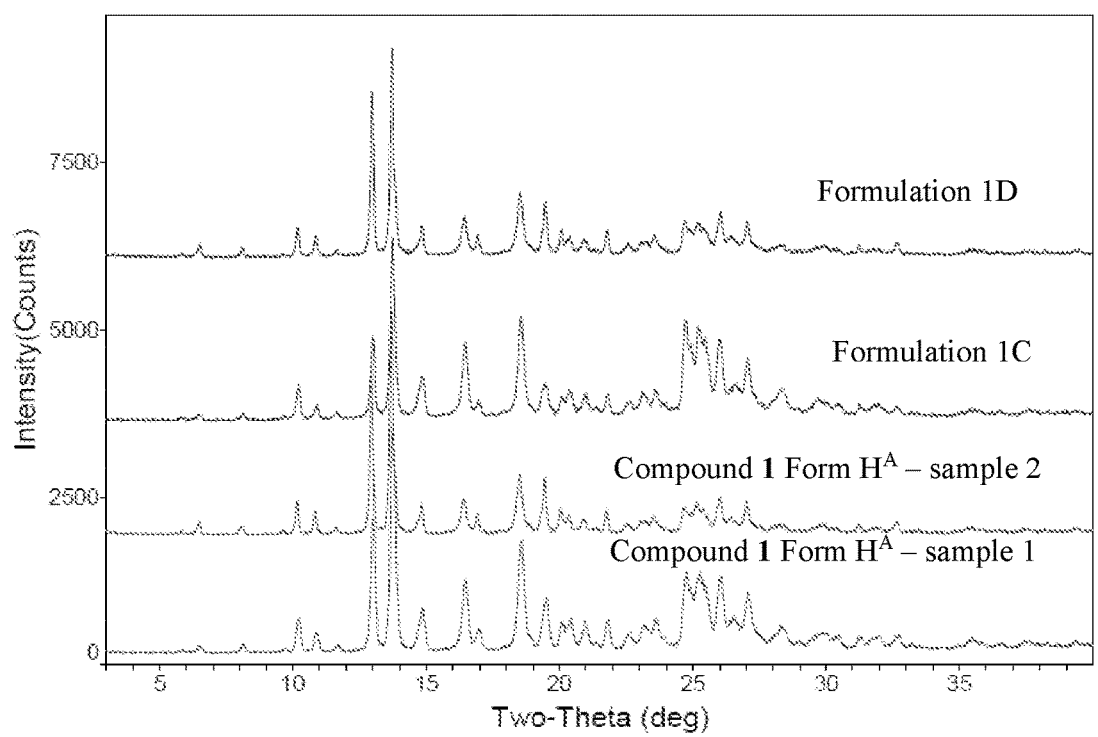
FIG. 1E depicts XRPD patterns for Formulation 1C, as compared to Compound 1 Form $H^A$ starting material.

Compound 1 Form $H^4$ (406 g) was added stepwise to the injector of a jetmill grinding system and micronized at a gas pressure setting of 3-4 bar with a feeding speed of about 10 g/hour. Two sub-lots (Formulations 1C and 1D) of micronized Compound 1 were collected and analyzed. PLM imagery and XRPD (FIG. 1E) analysis showed that both sub-lots of micronized Compound 1 remained crystalline and retained the same XRPD pattern as the Form $H^4$ starting material. The particle size distribution results showed $D_{10}$=~0.57 μm, $D_{50}$=~1.54 μm, and $D_{90}$=~4.48 m (pre- and post-grinding particle sizes shown in Table 1C). By HPLC analysis, the micronized powder was found to be 99.51% pure, which was identical to the starting material.

TABLE 1E

Characterization of larger scale micronized Compound 1 Form $H^4$ prepared by jetmill

| Formula No. | Appearance | PSD | | | XRPD | PLM | HPLC test Purity (%) |
| --- | --- | --- | --- | --- | --- | --- | --- |
| | | $D_{10}$ (μm) | $D_{50}$ (μm) | $D_{90}$ (μm) | | | |
| 1C | Off-white powder, electrostatic, agglomerated | 0.58 | 1.55 | 4.52 | No form change | Birefringence | 99.49 |
| 1D | | 0.57 | 1.54 | 4.48 | | | 99.43 |

1-Week and 4-Week Stability Studies of Formulation 1C

Figure 1F:
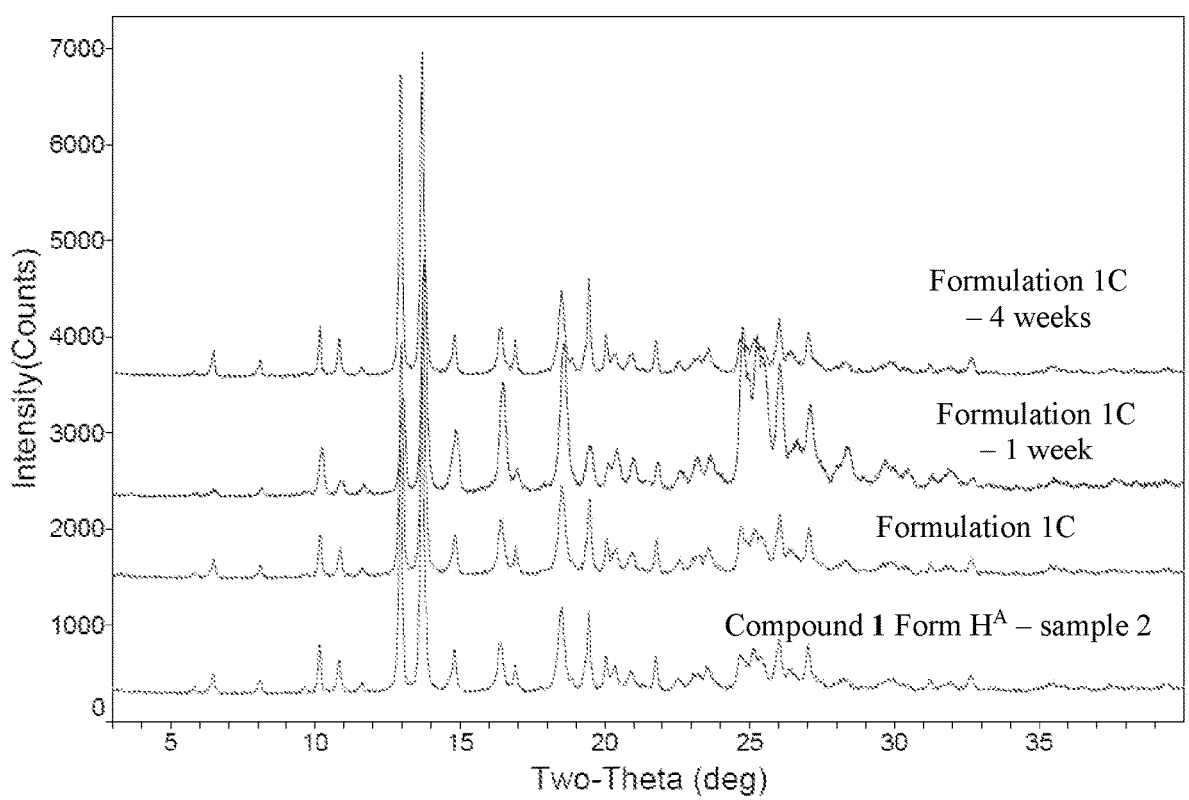
FIG. 1F depicts XRPD patterns for Formulation 1C after 1 week and 4 weeks stored at 25° C. and 60% relative humidity, as compared to Formula 1C before the stability study and Compound 1 Form $H^A$ starting material.

The chemical and physical stability of the micronized Formulation 1C were studied by placing the material in a 40-mL glass vial, covered by aluminum foil with pinholes and stored open under 25° C./60% RH for 1 week and 4 weeks. The 1-week and 4-week stability study results for Formulation 1C are reported below in Table 1F. XRPD spectra comparing the starting material and the micronized material after the 1 week and 4 week studies are shown in FIG. 1F.

PLM and XRPD patterns for Formulation C stored under 25° C./60% RH (open) for 1 week and 4 weeks both showed that the Compound 1 material remained crystalline with the same pattern as the unmilled starting material. The particle size distribution results showed comparable $D_{50}$ after 1 week and 4 weeks as both the initial 1C sample and 1D. The purity PLC results showed very little change, indicating that the micronized powder was chemically stable.

TABLE 1F 1 week and 4 week stability data of Formulation 1C

| Condition | Appearance | PSD | | | XRPD | PLM | HPLC test Purity (%) |
| --- | --- | --- | --- | --- | --- | --- | --- |
| | | $D_{10}$ (μm) | $D_{50}$ (μm) | $D_{90}$ (μm) | | | |
| initial | Off-white powder, electrostatic, agglomerated | 0.57 | 1.54 | 4.48 | No form change | Birefringence | 99.43 |

TABLE 1F-continued 1 week and 4 week stability data of Formulation 1C

| Condition | Appearance | PSD D$_{10}$ (μm) | PSD D$_{50}$ (μm) | PSD D$_{90}$ (μm) | XRPD | PLM | HPLC test Purity (%) |
|---|---|---|---|---|---|---|---|
| 25° C./60% RH, open, 1 W | Off-white powder, electrostatic, agglomerated | 0.57 | 1.41 | 4.14 | No form change | Birefringence | 99.52 |
| 25° C./60% RH, open, 4 W | Off-white powder, electrostatic, agglomerated | 0.59 | 1.66 | 4.97 | No form change | Birefringence | 99.50 |

Example 2: Dry Blend of Compound 1 Form H$^B$

Sample Preparation

Native Compound 1 Form H$^B$ (6 g), ground citric acid (1.5 g) and sodium lauryl sulfate (0.0075 g) were blended using a powder mixer-shaker for 45 minutes. The homogeneity of the sample after dry blending was analyzed by HPLC. The results are shown in Table 2A below. The Compound 1 load of the final blend was 80.0%, close to the feed drug load of 79.9%.

TABLE 2A

Drug load of Form H$^B$ after dry blend

| Formula No. | Appearance | Uniformity/HPLC | Drug load (%) |
|---|---|---|---|
| 2A | Off-white powder | 1 | 82.9 |
| | | 2 | 78.7 |
| | | 3 | 78.4 |
| | | Avg. | 80.0 |
| | | SD | 2.5 |

Example 3: Micronization of Compound 1 Form H$^A$ Blend

Sample Preparation

Compound 1 Form H$^A$ (10 g), PVP VA64 (0.3 g) and sodium lauryl sulfate (0.01 g) were blended using a powder mixer-shaker for 0.5 hour. The homogeneity of the sample after dry blending was analyzed by HPLC. The results are shown in Table 3A below. The Compound 1 load was 96.7%, close to the feed drug load of 96.9%.

TABLE 3A

Characterization of Compound 1 Form H$^A$ after Dry Blend

| Formula No. | Yield | Appearance | HPLC test | Drug load(%) |
|---|---|---|---|---|
| 3A | 100% | Off-white powder | 1 | 96.8 |
| | | | 2 | 97.1 |
| | | | 3 | 96.3 |
| | | | Avg. | 96.7 |
| | | | SD | 0.39 |

Micronization after Dry Blend

About 10 g of Formula 3A was added into the injector of a jetmill grinder and micronized with injector gas press of 3-4 bar. The micronized sample was collected and analyzed by XRPD, HPLC and PSD. The analysis summary is reported below in Table 3B.

Figure 2A:
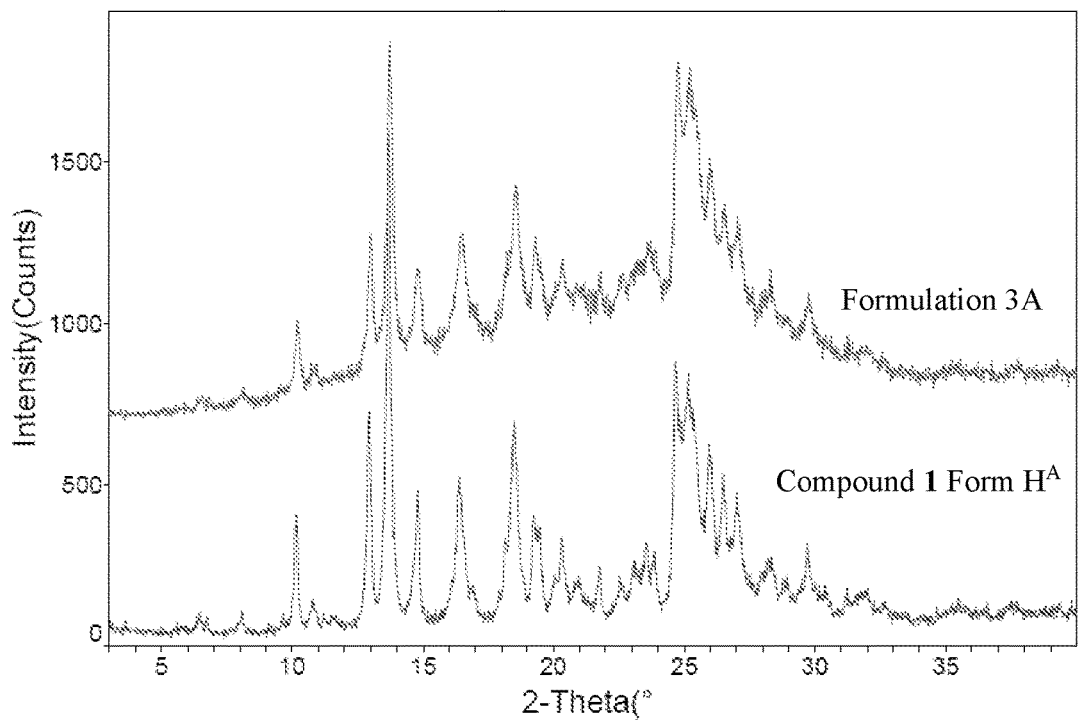
FIG. 2A depicts XRPD patterns for Formulation 3A after micronization, as compared to Compound 1 Form $H^A$ starting material.

According to the XRPD pattern (FIG. 2A), the micronized Formula 3A retained crystalline Compound 1 Form H$^A$ with the same pattern as the starting material. Particle size distribution analysis showed D$_{10}$=0.57 μm, D$_{50}$=1.59 μm, D$_{90}$=3.83 μm and a broad distribution profile with two peaks. HPLC results showed the Compound 1 drug load was 97.6%, close to the initial feed drug load of 96.9%, indicating the sample had good homogeneity. Compound 1 purity was almost the same as the starting material.

TABLE 3B

Characterization of Formula 3A after Micronization

| Formula No. | Yield | Appearance | PSD D$_{10}$ (μm) | | PSD D$_{50}$ (μm) | | PSD D$_{90}$ (μm) | | HPLC test Drug load (%) | | Purity (%) |
|---|---|---|---|---|---|---|---|---|---|---|---|
| 3A after micronization | 58.7% | Off-white powder, electrostatic | 1 | 0.57 | 1 | 1.61 | 1 | 3.90 | 1 | 97.5 | 1 98.79 |
| | | | 2 | 0.56 | 2 | 1.56 | 2 | 3.75 | 2 | 97.5 | 2 98.75 |
| | | | | | | | | | 3 | 97.7 | |
| | | | Avg. | 0.57 | Avg. | 1.59 | Avg. | 3.83 | Avg. | 97.6 | 3 98.79 |
| | | | | | | | | | SD | 0.15 | |

1-Week and 4-Week Stability Studies

Figure 2B:
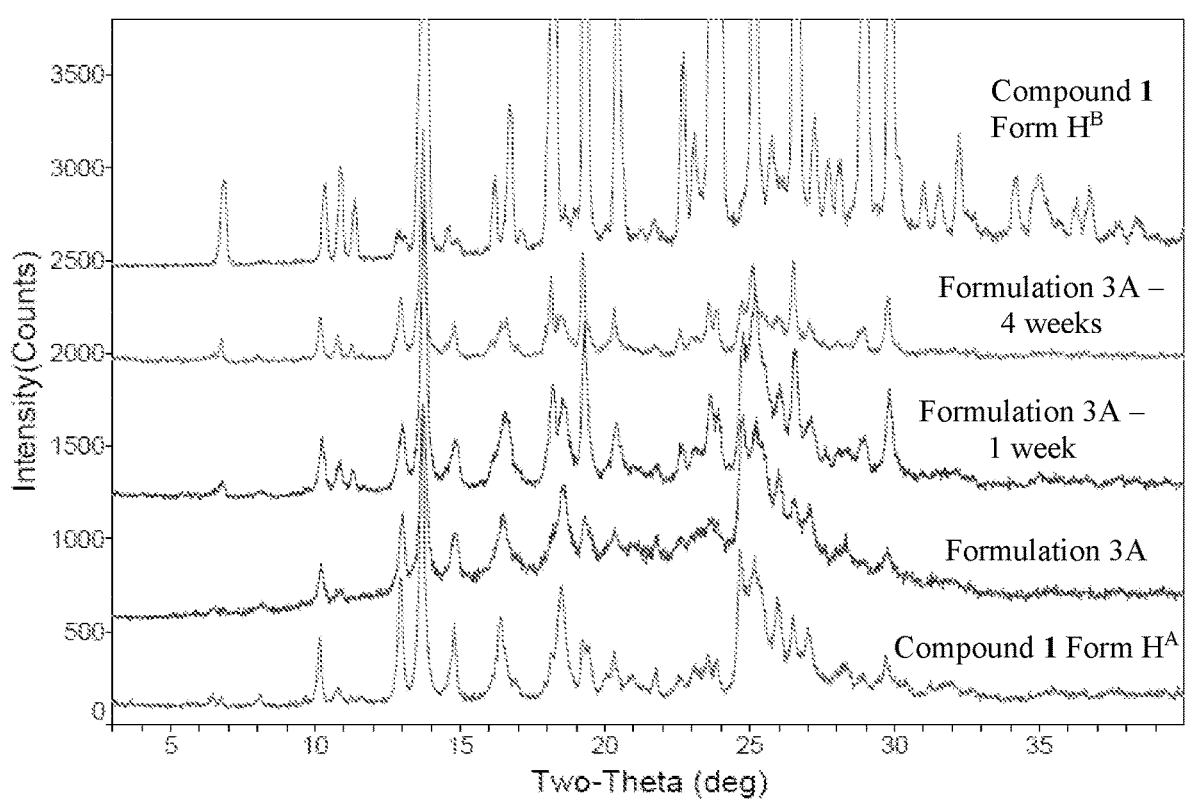
FIG. 2B depicts XRPD patterns for micronized Formulation 3A after 1 week and 4 weeks stored at 25° C. and 60% relative humidity, as compared to micronized Formula 3A before the stability study, Compound 1 Form $H^B$ starting material and Compound 1 Form $H^A$.

The chemical and physical stability of the micronized Formula 3A was studied by placing the material in a 40-mL glass vial, covered by aluminum foil with pinholes and stored open under 25° C./60% RH for 1 week and 4 weeks. The 1-week and 4-week stability study results for Formulation 3A are reported below in Table 3C. XRPD spectra comparing the starting material and the micronized material after the 1 week and 4 week studies are shown in FIG. 2B.

PLM and XRPD patterns for Formulation 3A stored under 25° C./60% RH (open) for 1 week and 4 weeks both showed that the Compound 1 material remained crystalline but appeared to be a mixture of Form $H^A$ and a minor amount of Form $H^B$. The particle size distribution results showed minor changes in $D_{50}$ after 1 week and 4 weeks. The purity HPLC results showed very little change, indicating that the micronized powder was chemically stable.

Example 4: Scaled-Up Preparation for Micronized Form $H^B$

Pilot Sample Preparation and Characterization

Compound 1 Form $H^B$ (20 g) was added stepwise to the injector of a jetmill grinding system and micronized at a gas pressure setting of 3-4 bar in 2 hours. The micronized powder (Formula 4A) was collected (79.3% yield) and characterized by PLM, XRPD, HPLC and PSD analysis.

Figure 3A:
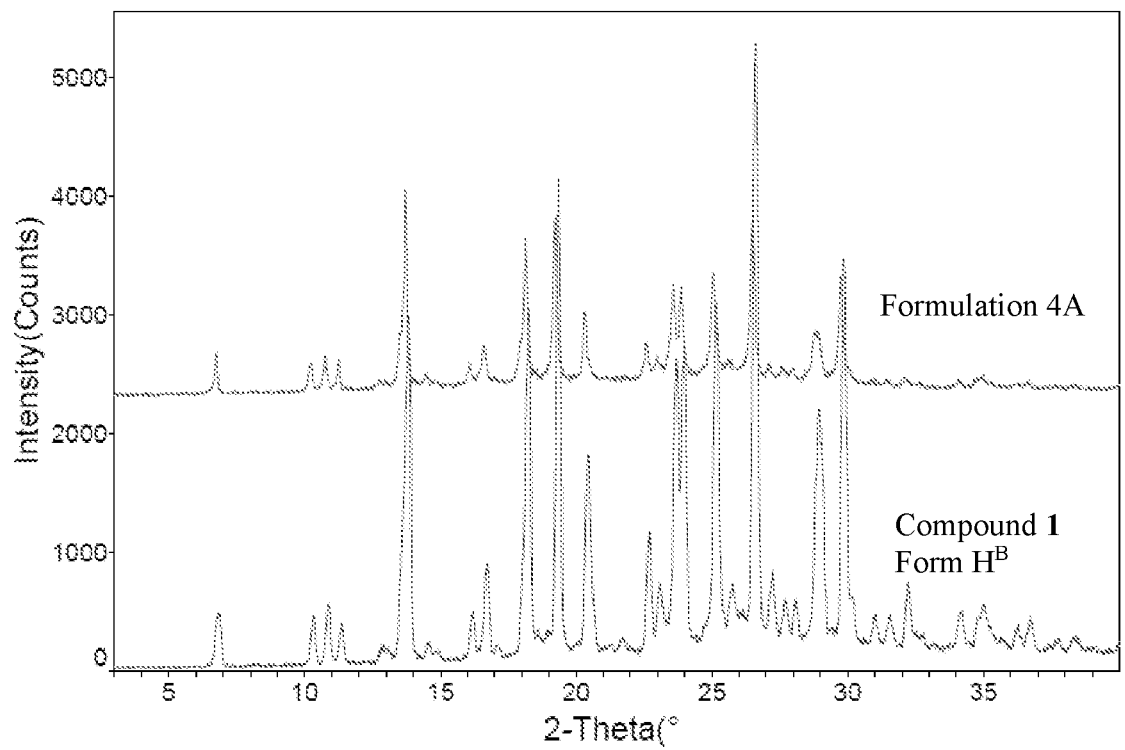
FIGS. 3A, 3B and 3C depict XRPD patterns for Formulations 4A, 4B and 4C, respectively, as compared to Compound 1 Form $H^B$ starting material.

According to the PLM images and XRPD pattern (FIG. 3A), the micronized formulation 4A retained crystalline Compound 1 Form $H^B$ with the same pattern as the starting material, but the intensity of the characteristic diffraction peaks decreased due to a smaller particle size. Particle size distribution analysis showed $D_{10}$=0.66 μm, $D_{50}$=2.45 μm and $D_{90}$=5.53 μm. HPLC results showed the purity of micronized Compound 1 was 98.80%, almost the same as the starting material (98.3%). The material appeared to be an off-white powder, which was electrostatic and agglomerated.

TABLE 4A

Characterization of scaled up Form $H^B$ micronized powder

| Formula No. | | $D_{10}$ (μm) | | PSD $D_{50}$ (μm) | | $D_{90}$ (μm) | XRPD | PLM | HPLC test Purity (%) |
|---|---|---|---|---|---|---|---|---|---|
| 4A | 1 | 0.67 | 1 | 2.51 | 1 | 5.61 | No form change | Birefringence | 98.80 |
| | 2 | 0.64 | 2 | 2.38 | 2 | 5.44 | | | |
| | Avg. | 0.66 | Avg. | 2.45 | Avg. | 5.53 | | | |

400 g-Scale Micronization

Compound 1 Form $H^B$ was added to a jetmill grinding system and micronized at a gas pressure setting of 3-4 bar and 3 bar with a feeding speed of 10 g/hour. The micronized powder was collected in two lots (Formulas 4B and 4C) and characterized by PLM, XRPD, HPLC and PSD analysis.

Figure 3B:
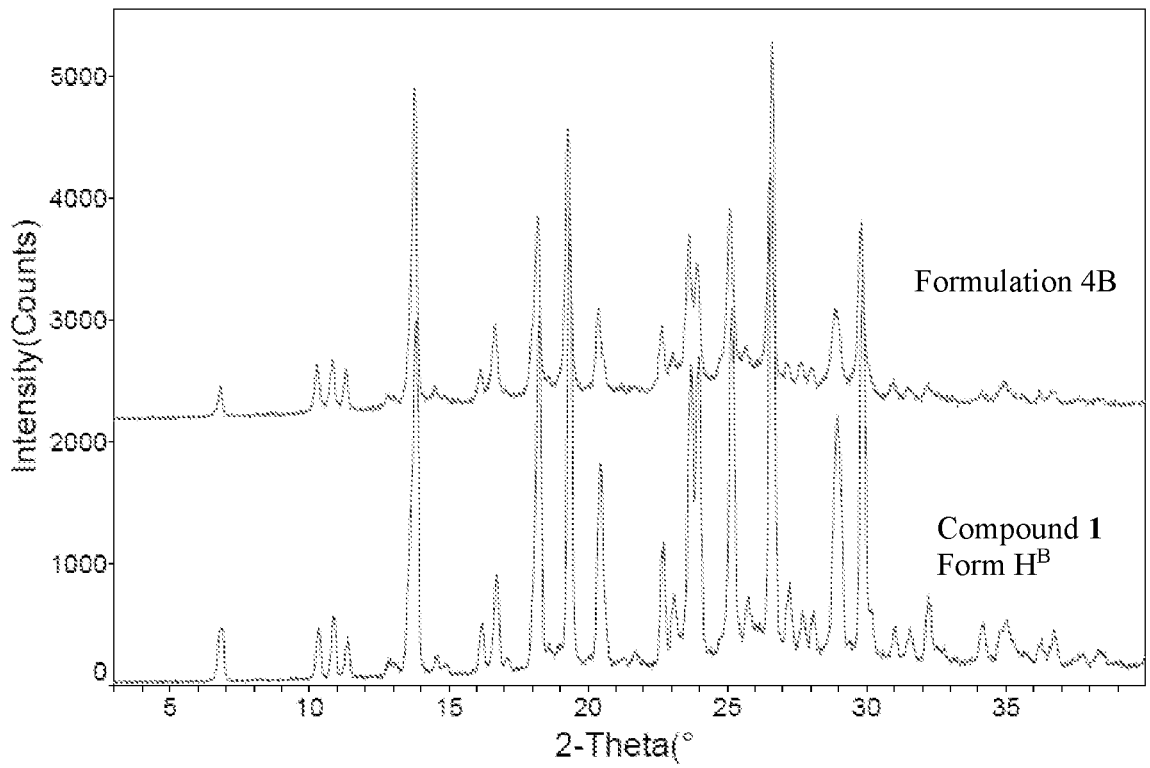
Figure 3C:
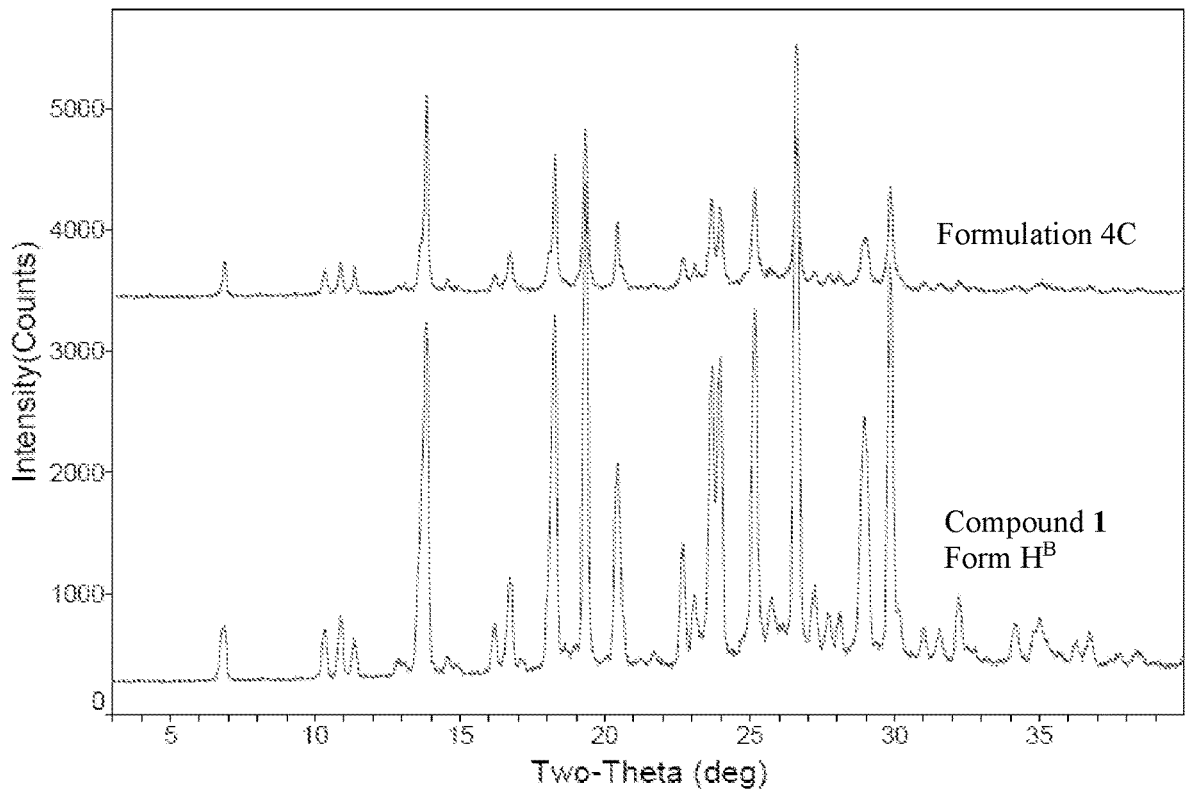

According to the PLM images and XRPD pattern (FIGS. 3B and 3C), micronized Formulas 4B and 4C retained crystalline Compound 1 Form $H^B$ with the same pattern as the starting material. Particle size distribution analysis showed $D_{10}$=0.67 μm, $D_{50}$=2.48 μm and $D_{90}$=5.49 μm for the first lot (4B) and $D_{10}$=0.65 μm, $D_{50}$=2.25 μm and $D_{90}$=4.91 μm for the second lot (4C). HPLC results showed the purity of micronized Compound 1 was 98.69% and 98.67%, respectively, almost the same as the starting material (98.3%). Both lots of the material appeared to be an off-white powder, which was electrostatic and agglomerated.

TABLE 4B

Characterization of scaled up Form $H^B$ micronized powder

| Batch No. | | $D_{10}$ (μm) | | PSD $D_{50}$ (μm) | | $D_{90}$ (μm) | XRPD | PLM | HPLC test Purity (%) |
|---|---|---|---|---|---|---|---|---|---|
| 4B | 1 | 0.67 | 1 | 2.42 | 1 | 5.41 | No form change | Birefringence | 98.69 |
| | 2 | 0.68 | 2 | 2.59 | 2 | 5.67 | | | |
| | 3 | 0.67 | 3 | 2.42 | 3 | 5.39 | | | |
| | Avg. | 0.67 | Avg. | 2.48 | Avg. | 5.49 | | | |
| 4C | 1 | 0.65 | 1 | 2.22 | 1 | 4.83 | No form | Birefringence | 98.67 |
| | 2 | 0.66 | 2 | 2.34 | 2 | 5.04 | | | |

TABLE 4B-continued

Characterization of scaled up Form $H^B$ micronized powder

| Batch No. | PSD | | | | | | XRPD | PLM | HPLC test Purity (%) |
|---|---|---|---|---|---|---|---|---|---|
| | $D_{10}$ (μm) | | $D_{50}$ (μm) | | $D_{90}$ (μm) | | | | |
| 3 | 0.66 | 3 | 2.33 | 3 | 5.1 | | change | | |
| 4 | 0.64 | 4 | 2.11 | 4 | 4.65 | | | | |
| Avg. | 0.65 | Avg. | 2.25 | Avg. | 4.91 | | | | |

Example 5: Additional Blended Formulations of Compound 1 Form $H^B$

Dry Granulation Via Roller Compaction

The powdered ingredients listed in Tables 5A and 5B, except for magnesium stearate, were screened with 30 mesh (600 m) sieve and mixed using a V-blender at 25 rpm for 2 minutes. The magnesium stearate was screened through a 40 mesh (425 m) sieve and mixed with unlubricated pre-mix using a V-blender at 25 rpm for 2 minutes. Using a TFC-Lab roller compactor (Vector Corporation) ribbons having a thickness about 1 mm were obtained using a roll force of 500 psi, roll speed 3 rpm, and screw feeder speed 30 rpm. The ribbons were granulated using a 20 mesh (850 m) sieve.

Processing via dry granulation involved no solvents and minimized heat exposure for Compound 1. The small-scale prototypes were prepared by roller compaction. The following formulations also include surfactant and acidifier to attempt to improve solubility (Tables 5A-5B).

TABLE 5A

Dry Granulation Formulation 5A

| Ingredient | % w/w | g/batch |
|---|---|---|
| Compound 1 Form $H^B$ | 50 | 25 |
| Microcrystalline cellulose 102 | 15 | 7.5 |
| Dicalcium phosphate | 14 | 7 |
| Ascorbic acid | 10 | 5 |
| Poloxamer 188 | 5 | 2.5 |
| Sodium starch glycolate | 5 | 2.5 |
| Magnesium stearate | 1 | 0.5 |
| Total: | 100 | 50 |

TABLE 5B

Dry Granulation Formulation 5B

| Ingredient | % w/w | g/batch |
|---|---|---|
| Compound 1 Form $H^B$ | 50 | 25 |
| Microcrystalline cellulose 102 | 15 | 7.5 |
| Lactose monohydrate 316 | 14 | 7 |
| Citric acid | 10 | 5 |
| Sodium lauryl sulfate | 5 | 2.5 |
| Crospovidone XL-10 | 5 | 2.5 |
| Magnesium stearate | 1 | 0.5 |
| Total: | 100 | 50 |

Wet Granulation Formulations

The powdered ingredients listed in Tables 5C and 5D were screened with a 30 mesh sieve and mixed using a V-blender at 25 rpm for 2 minutes. The mixture was transferred to a L GMX bowl and granulated with an alcoholic solution at mixer/chopper speed 250/1800 rpm. The solvent was removed by evaporation at room temperature. The dry material was granulated using an 18 mesh (1000 μm) sieve.

Formulations 5C and 5D were processed via a modified 'wet granulation' approach using a high shear granulator. In the preparation of Formulation 5C, to avoid heat exposure the molten semi-solid excipients (e.g., Gelucire, Vitamin E TPGS, Peceol) were dissolved in methanol and the solution was used as a granulation liquid for incorporation of the solid phase. In the preparation of Formulation 5D, the liquid surfactant (Polysorbate 80) was first dissolved in ethanol and the solution was used as a granulation liquid.

TABLE 5C

Modified Wet Granulation Formulation 5C

| Ingredient | % w/w | g/batch |
|---|---|---|
| Compound 1 Form $H^B$ | 50 | 25 |
| Mannitol 160 | 22.5 | 11.25 |
| Microcrystalline cellulose 101 | 15 | 7.5 |
| Gelucire 44/14 | 5 | 2.5 |
| Vit. E TPGS | 5 | 2.5 |
| Peceol | 0.5 | 0.25 |
| Colloidal silicon dioxide | 2 | 1 |
| Methanol | (30) | (15) |
| Total: | 100 | 50 |

(#) evaporated at RT

TABLE 5D

Wet Granulation Formulation 5D

| Ingredient | % w/w | g/batch |
|---|---|---|
| Compound 1 Form $H^B$ | 50 | 25 |
| Mannitol 160 | 15 | 7.5 |
| Microcrystalline cellulose 101 | 13 | 6.5 |
| Tartaric acid | 10 | 5 |
| Polysorbate 80 | 5 | 2.5 |
| Croscarmellose sodium | 5 | 2.5 |
| Povidone K-29/32 | 2 | 1 |
| Ethanol | (30) | (15) |
| Total: | 100 | 50 |

(#) evaporated at RT

Amorphous Co-Precipitation by Spray-Drying

Compound 1 Form $H^B$ was dissolved in 400 mL of solvent (Formulation 5E=MeOH/DCM 1:1 v/v; Formulations 5F and 5G=MeH). The solutions were filtered to remove undissolved material. After filtering 100 and 400 mL of DCM were added to clear Formulations 5F and 5G, respectively. Polymer and surfactant (as outlined in Tables 5E-5G) were then added and dissolved. The solutions were spray-dried at 20±2 g/min, inlet temperature 65° C., atomization pressure 0.15 MPa, and air flow 0.4 m³/min, using a Yamato Lab Spray Dryer Model GB22 with internal nozzle diameter 711 μm. After all the solution was sprayed the heating was maintained for 10 minutes at 65° C. The spray dried material was kept overnight in the fume hood.

TABLE 5E

Spray-Dried Dispersion Formulation 5E

| Ingredient | % w/w solids | g/batch |
|---|---|---|
| Compound 1 Form $H^B$ | 40 | 10 |
| Povidone K-29/32 | 55 | 13.75 |
| Polysorbate 80 | 5 | 1.25 |
| DCM/MeOH 20/80 v/v | — | (625) |
| Total: | 100 | 25 |

TABLE 5F

Spray-Dried Dispersion Formulation 5F

| Ingredient | % w/w solids | g/batch |
|---|---|---|
| Compound 1 Form $H^B$ | 40 | 10 |
| HPMC-AS | 55 | 13.75 |
| SLS | 5 | 1.25 |
| DCM/MeOH 50/50 v/v | — | (850) |
| Total: | 100 | 25 |

TABLE 5G

Spray-Dried Dispersion Formulation 5G

| Ingredient | % w/w solids | g/batch |
|---|---|---|
| Compound 1 Form $H^B$ | 40 | 10 |
| Povidone K-29/32 | 55 | 13.75 |
| SLS | 5 | 1.25 |
| DCM/MeOH 50/50 v/v | — | (500) |
| Total: | 100 | 25 |

Additional Amorphous Co-Precipitation by Spray-Drying—Formulation 5H

Figure 4A:
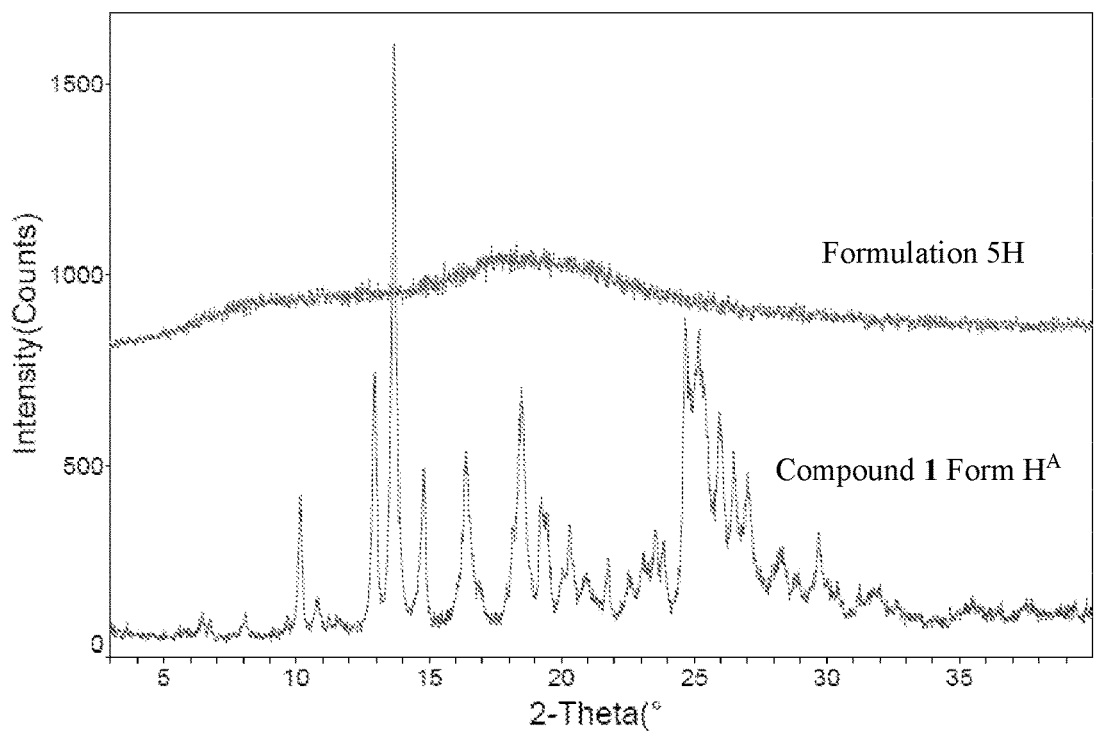
FIG. 4A depicts XRPD patterns for Formulation 5H, as compared to Compound 1 Form $H^A$ starting material.

Compound 1 Form $H^A$, Eudragit EPO and HPMC E3 (25/37.5/37.5 by wt %) were added to a glass vial and 1.6 L of MeOH:H₂O (90:10 v/v) were added, and the solids were dissolved completely by sonication and magnetic stirring to obtain clear solution with a target Compound 1 concentration of about 5 mg/mL. The solution was spray-dried using a BUCHI B290 spray drier with a 0.7 mm nozzle, inlet temperature of 110° C., outlet temperature of 42-58° C., aspirator set to 100%, pump set to 55% and Q-flow of 45 MPa. The products were collected and dried under vacuum at 30° C. for 16 hours. The spray dried material was characterized by PLM, SEM, XRPD, HPLC and mDSC test. According to PLM images and XRPD patterns (FIG. 4A), an amorphous solid dispersion, Formulation 5H, was produced. According to the HPLC results, the drug load was determined to be 26.1%, and the purity was about 98.6%, the same as starting material. The mDSC result showed a glass transition at 100° C.

Figure 4B:
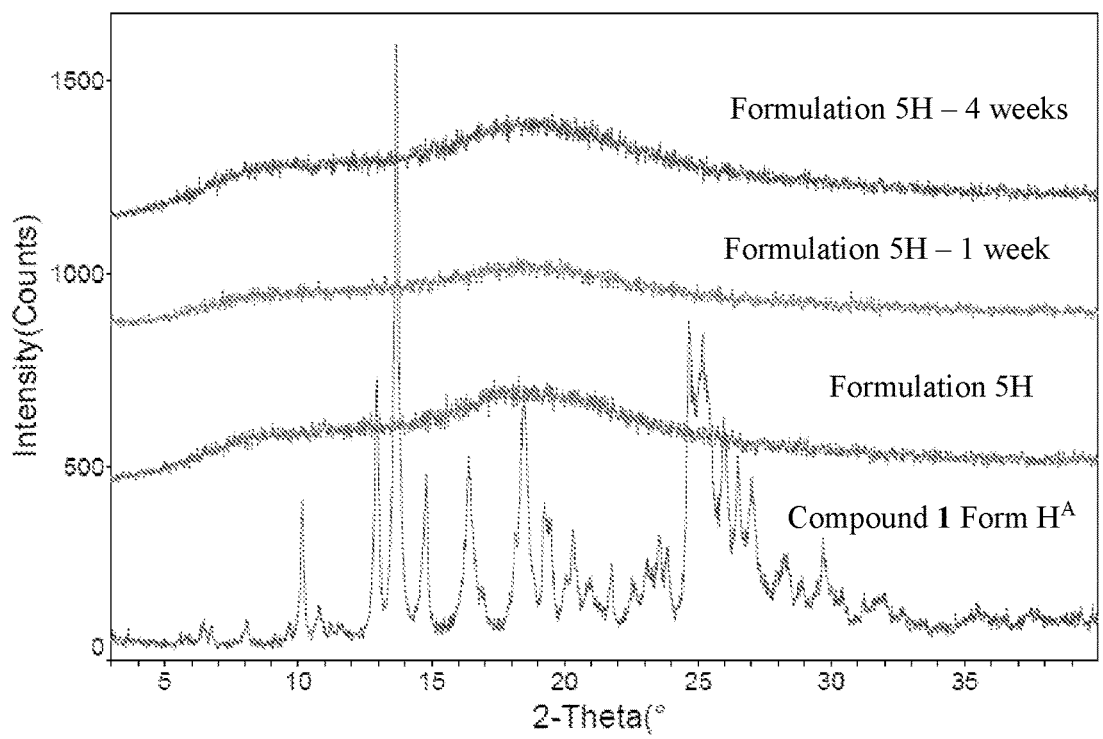
FIG. 4B depicts XRPD patterns for Formulation 5H after 1 week and 4 weeks stored at 25° C. and 60% relative humidity, as compared to Formula 5H before the stability study and Compound 1 Form $H^A$ starting material.

The chemical and physical stability of Formulation 5H was studied by placing the material in a 40-mL glass vial, covered by aluminum foil with pinholes and stored open under 25° C./60% RH for 1 week and 4 weeks. The 1-week and 4-week stability study results for Formulation 5H are reported below in Table 5H. XRPD spectra comparing the starting material and the micronized material after the 1 week and 4 week studies are shown in FIG. 4B.

PLM and XRPD patterns for Formulation 5H stored under 25° C./60% RH (open) for 1 week and 4 weeks both showed that the Compound 1 material remained amorphous. The samples displayed a glass transition temperature of 93° C. after 1 week and 110° C. after 4 weeks. The purity HPLC results showed very little change.

TABLE 5H

Initial and 1-week and 4-week stability test results of Formulation 5H

| | | | | HPLC test | | | |
|---|---|---|---|---|---|---|---|
| Condition | Appearance | XRPD | mDSC (Tg, ° C.) | Drug load (%) | | Purity (%) | |
| Initial | Off-white powder, electrostatic, no agglomerated | Amorphous | 100 | 1<br>2<br>3<br>Avg. | 26.1<br>26.2<br>26.1<br>26.1 | 1<br>2<br>3<br>N/A | 98.52<br>98.68<br>98.66<br>N/A |
| 25° C./60% RH, open, 1 Week | Off-white powder, electrostatic, no agglomerated | Amorphous | 93 | N/A | | 98.74 | |
| 25° C./60% RH, open, 4 Weeks | Off-white powder, electrostatic, no agglomerated | Amorphous | 110 | N/A | | 98.73 | |

Drug Products 50 mg Compound 1 Form $H^B$ capsules were prepared by filling the final blends into size 0 HPMC capsules. The weight of filled final blends was corrected by API purity (98.68%).

TABLE 5I 50 mg Compound 1 Form HB capsules

| Lot No. | Formulation | Composition | Filling weight (mg) |
|---|---|---|---|
| X1 | 5A | Micronized Compound 1 Form $H^B$ (50%), Tabulose 102 (15%), Dicalcium phosphate (14%), Ascorbic acid (10%), Poloxamer 188 (5%), Sodium starch glycolate (5%), Magnesium stearate (1%) | 101.3 |

TABLE 5I-continued 50 mg Compound 1 Form HB capsules

| Lot No. | Formulation | Composition | Filling weight (mg) |
|---|---|---|---|
| X2 | 5B | Micronized Compound 1 Form $H^B$ (50%), Tabulose 102 (15%), Lactose 316 (14%), Citric acid (10%), SLS (5%), Crospovidone XL-10 (5%), Magnesium stearate (1%) | 101.3 |
| X3 | 5C | Micronized Compound 1 Form $H^B$ (50%), Mannitol 160C (22.5%), Tabulose 101 (15%), Tartaric acid (10%), Gelucire 44/14 (5%), Vit. E TPGS (5%), Peceol (0.5%), Colloidal silicon dioxide (2%) | 101.3 |
| X4 | 5D | Micronized Compound 1 Form $H^B$ (50%), Mannitol 160C (15%), Tabulose 101 (13%), Tartaric acid (10%), Polysorbate 80 (5%), Croscarmellose sodium (5%), Plasdone 29/32 (2%) | 101.3 |
| X5 | 5E | Micronized Compound 1 Form $H^B$ (40%), Plasdone 29/32 (55%), Polysorbate 80 (5%) | 126.7 |
| X6 | 5F | Micronized Compound 1 Form $H^B$ (40%), HPMCAS-MF (55%), SLS (5%) | 126.7 |
| X7 | 5G | Micronized Compound 1 Form $H^B$ (40%), Plasdone 29/32 (55%), SLS (5%) | 126.7 |
| X8 | 4A | Micronized Compound 1 Form $H^B$ (100%) | 50.7 |
| X9 | 2A | Native Micronized Compound 1 Form $H^B$ (79.9%), citric acid (20.0%), and sodium lauryl sulfate (0.1%) | 62.6 |
| X21 | 5H | Compound 1 Form $H^4$ (25%), Eudragit EPO (37.5%) and HPMC E3 (37.5%) | ~300 |

Stability Study

Spray dried Formulations 5E, 5F and 5G and capsule lot X7 were stored their original preparation vials at 2-8° C./75-95% RH, in 40 cc HDPE closed (but not sealed) bottles at 40° C./75% RH or in 15×45 mm glass bottles with polyvinyl lined caps at 25° C./60% RH for up to 4 weeks. Each of Formulations 5E, 5F and 5G were found to contain amorphous Compound 1 at the start of the stability study.

Samples of Formulation 5E crystallized under the 40° C./75% RH conditions after 1 week and at the 2-8° C./75-95% RH after 3 weeks, but samples stored at 25° C./60% RH remained amorphous. Samples of Formulation 5F did not show any crystallization of API, but did show minor crystalline reflections due to sodium lauryl sulfate. Samples of Formulation 5G crystallized under the 40° C./75% RH conditions after 2 weeks, but capsule lot X7 did not, and both Formulation 5G and capsule lot X7 remained amorphous at the 25° C./60% RH and 2-8° C./75-95% RH conditions.

Volatile Content Analysis

For the formulations involving solvents, the volatile content (water content and residual solvent) was estimated by LOD and TGA (Table 5J).

Samples of Formulations 5C and 5D were dried at RT overnight. Povidone containing Formulations 5E and 5G showed a volatile content of about 4% after spray-drying and increased to about 5% when exposed to ambient air. This is likely the result of hygroscopicity of povidone which typically contains 5% water content. Formulation 5F showed a weight loss by TGA between 20-120° C. of about 1% and no overnight water uptake was observed.

TABLE 5J

Volatile Content Analysis of Formulations 5C-5G

| Formulation | Solvent | Technique | Initial (%) | Final (%) |
|---|---|---|---|---|
| 5C | MeOH (100%) | LOD | 2.5 | 2.7 |
| 5D | EtOH (100%) | | 4.3 | 3.3 |
| 5E | MeOH/DCM (80:20 v/v) | TGA | — | 4.5/4.5* |
| 5F | MeOH/DCM (50:50 v/v) | | — | 1.1/1.1* |
| 5G | | | — | 3.8/4.8* |

*(after spray-drying/after overnight drying in a fume hood)

Example 6: Additional Blended Formulations of Compound 1 Form $H^4$

Dry Blend Formulations

Dry blends Formulations 6A-6D were prepared using a 0.5 qt V-blender. The powders were screened through a 30 mesh sieve. The excipients were first mixed for 2 minutes at 25 rpm and then Compound 1 Form $H^4$ was added and mixed for 4 minutes.

TABLE 6A

Dry Blend Formulation 6A

| Ingredient/Function | % w/w | g/batch |
|---|---|---|
| Compound 1 Form $H^4$/API | 50 | 15 |
| HPMC-AS/Filler | 20 | 6 |
| Citric acid/Acidulant | 15 | 4.5 |
| Sodium lauryl sulfate/Surfactant | 15 | 4.5 |
| Total: | 100 | 30 |

TABLE 6B

Dry Blend Formulation 6B

| Ingredient/Function | % w/w | g/batch |
|---|---|---|
| Compound 1 Form $H^4$/API | 50 | 15 |
| Pregel starch 1500/Filler | 20 | 6 |
| Citric acid/Acidulant | 15 | 4.5 |
| Sodium lauryl sulfate/Surfactant | 15 | 4.5 |
| Total: | 100 | 30 |

TABLE 6C

Dry Blend Formulation 6C

| Ingredient/Function | % w/w | g/batch |
|---|---|---|
| Compound 1 Form $H^4$/API | 50 | 15 |
| Citric acid/Acidulant | 50 | 15 |
| Total: | 100 | 30 |

TABLE 6D

Dry Blend Formulation 6D

| Ingredient/Function | % w/w | g/batch |
|---|---|---|
| Compound 1 Form $H^4$/API | 50 | 15 |
| Citric acid/Acidulant | 45 | 13.5 |
| Sodium lauryl sulfate/Surfactant | 5 | 1.5 |
| Total: | 100 | 30 |

Dry Granulation via Roller Compaction

Dry granulation formulations 6E and 6F of Compound 1 Form $H^4$ were prepared as described in Example 5.

TABLE 6E

Dry Granulation Formulation 6E

| Ingredient/Function | % w/w | g/batch |
|---|---|---|
| Compound 1 Form $H^4$/API | 50 | 15.0 |
| Microcrystalline cellulose 102/Filler | 10 | 3.0 |
| Lactose monohydrate 316/Filler | 10 | 3.0 |
| Citric acid/Acidulant | 12.5 | 3.8 |
| Sodium lauryl sulfate/Surfactant | 12.5 | 3.8 |
| Croscarmellose sodium/Disintegrant | 4.5 | 1.4 |
| Magnesium stearate/Lubricant | 0.5 | 0.2 |
| Total: | 100 | 30 |

TABLE 6F

Dry Granulation Formulation 6F

| Ingredient/Function | % w/w | g/batch |
|---|---|---|
| Compound 1 Form $H^4$/API | 50 | 15.0 |
| Microcrystalline cellulose 102/Filler | 10 | 3.0 |
| Dicalcium phosphate/Filler | 10 | 3.0 |
| Citric acid/Acidulant | 12.5 | 3.8 |
| Poloxamer 407/Surfactant | 12.5 | 3.8 |
| Sodium starch glycolate/Disintegrant | 4.5 | 1.4 |
| Magnesium stearate/Lubricant | 0.5 | 0.2 |
| Total: | 100 | 30 |

Drug Products

Final blends from Formulations 6A-6F were filled into gelatin capsules (Tables 6G and 6H). The size of the capsule was chosen depending on blend density.

TABLE 6G 50 mg Compound 1 Form $H^4$ capsules

| Ingredient | Formulation 6A Caps size "2" Lot X10 | Formulation 6B Caps size "2" Lot X11 mg/unit | Formulation 6C Caps size "4" Lot X12 |
|---|---|---|---|
| Compound 1 Form $H^4$ | 50 | 50 | 50 |
| HPMC-AS | 20 | — | — |
| Pregel Starch 1500 | — | 20 | — |
| Citric acid | 15 | 15 | 50 |
| Sodium lauryl sulfate | 15 | 15 | 12.5 |
| Microcrystalline cellulose | — | — | 10 |
| Lactose monohydrate | — | — | 10 |
| Croscarmellose sodium | — | — | 4.5 |
| Magnesium stearate | — | — | 0.5 |
| Total: | 100 | 100 | 100 |

TABLE 6H 50 mg Compound 1 Form $H^4$ capsules

| Ingredient | Formulation 6D Caps size "2" Lot X13 | Formulation 6E Caps size "4" Lot X14 mg/unit | Formulation 6F Caps size "4" Lot X15 |
|---|---|---|---|
| Compound 1 Form $H^4$ | 50 | 50 | 50 |
| Citric acid | 45 | 12.5 | 12.5 |
| Sodium lauryl sulfate | 5 | 12.5 | — |
| Poloxamer 407 | — | — | 12.5 |
| Microcrystalline cellulose | — | 10 | 10 |
| Lactose monohydrate | — | 10 | — |
| Dicalcium phosphate | — | — | 10 |
| Croscarmellose sodium | — | 4.5 | — |
| Sodium starch glycolate | — | — | 4.5 |
| Magnesium stearate | — | 0.5 | 0.5 |
| Total: | 100 | 100 | 100 |

Other Formulations

Additional capsules were formulated and placed in size 0 HPMC capsules.

TABLE 6I 50 mg Compound 1 Form $H^4$ capsules

| Lot No. | Formulation | Composition | Filling weight (mg) |
|---|---|---|---|
| X16A | 1A | Micronized Compound 1 Form $H^4$ | 50.0 |
| X16B | 1C | Micronized Compound 1 Form $H^4$ | 50.0 |
| X17 | 3A | Co-micronized Compound 1 Form $H^4$ (96.9%), Kollidon VA 64 (3.0%), and sodium lauryl sulfate (0.1%) | 51.6 |

Placebo and API Test Formulations

Placebo formulation 6G and Compound 1 Form $H^4$ formulation 6H were prepared at 500 and 100 g scale, respectively. The powders were screened through a 35 mesh sieve (0.5 mm opening) and mixed for 5 minutes using a V-blender at 25 rpm. The final formulation 6I blend was filled into gelatin capsules at different drug dose (Table 6L).

TABLE 6J

Placebo Formulation 6G

| Ingredient | % w/w | g/batch |
|---|---|---|
| Microcrystalline cellulose 102, USP/NF, EP, Tabulose 102, Blanver | 50 | 250 |
| Citric Acid Anhydrous FG, USP, FCC, ADM | 45 | 225 |
| Sodium Lauryl Sulfate, EP, JP, NF/USP, Stepanol WA-100 NF/USP, Stepan | 5 | 25 |
| Total: | 100 | 500 |

TABLE 6K

Dry Blend Compound 1 Form H[4] Formulation 6H

| Ingredient | % w/w | g/batch |
|---|---|---|
| Compound 1 Form H[4] | 50 | 50 |
| Citric Acid Anhydrous FG, USP, FCC, ADM | 45 | 45 |
| Sodium Lauryl Sulfate, EP, JP, NF/USP, Stepanol WA-100 NF/USP, Stepan | 5 | 5 |
| Total: | 100 | 100 |

TABLE 6L

Formulation 6H Capsules Lots

| Lot No. | Compound 1 Dose (mg) | Preparation |
|---|---|---|
| X18 | 3 | 6 mg blend in size 3 Gelatin capsules |
| X19 | 50 | 100 mg blend in size 1 Gelatin capsules |
| X20 | 125 | 250 mg blend in size 0 Gelatin capsules |

Stability Study

The chemical stability of Formulation 6B was evaluated for samples stored in open and closed vial at 40° C./75% RH. A summary of the results is shown in Table 6M.

A significant change in appearance was observed for the samples stored in an open vial at 40° C./75% RH, from an off-white powder (initial sample) to a gray paste in presence of high humidity exposure. The change in appearance of samples stored in open vials was likely the result of moisture absorption over time. The impurity profile observed in samples throughout the stability study was equivalent to that of the API concurrently analyzed. The bulk blend was chemically stable for at least 3 months when stored in closed vials (Table 6M).

Figure 5:
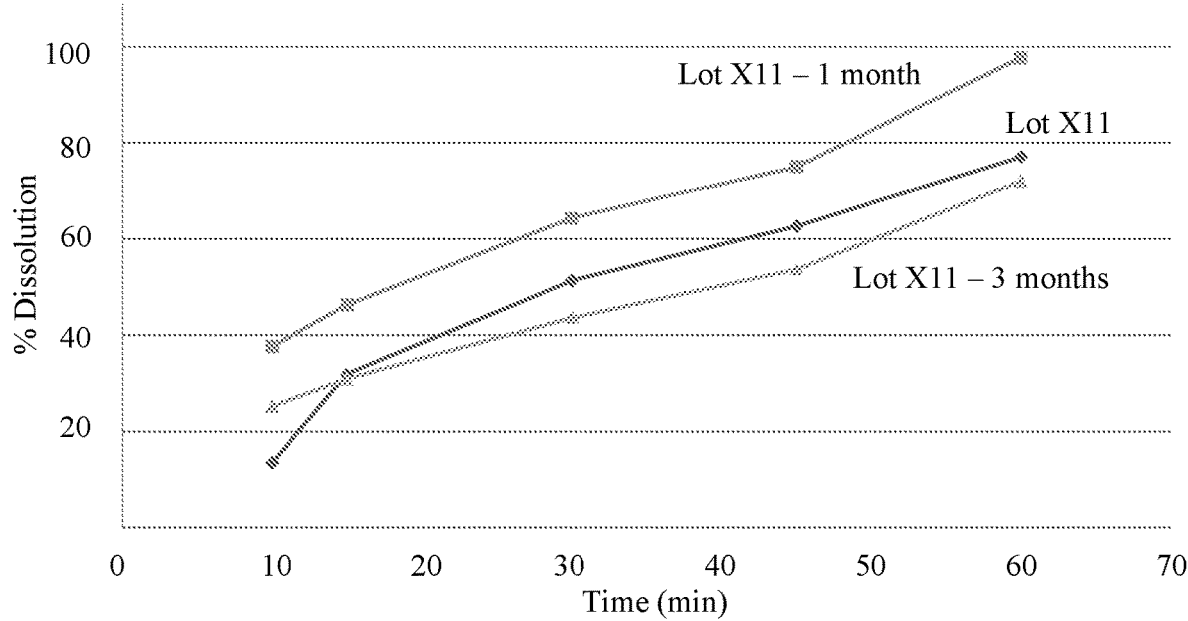
FIG. 5 depicts a dissolution profile for Capsule Lot X11 containing Formulation 6B, comparing fresh Formulation 6B and after 1 month and 3 months of storage at 40° C./75% RH

The dissolution profiles of the 50 mg Formulation 6B Lot X11 capsule are illustrated in FIG. 5. Faster and complete release was observed from the capsules stored at 40° C./75% RH for 1 month. A slower release profile was obtained from the capsules stored at 40° C./75% RH for 3 months when compared to the profile of the capsules tested after 1 month of storage. A colloidal mass was observed inside the sinker at the end of the dissolution. This result was not observed in the samples after 1 month of storage.

TABLE 6M

Impurity Profile of Formulation 6B after Stability Study

| Storage conditions | 25° C./60% RH closed vial | | 40° C./75% RH open vial | | 40° C./75% RH closed vial | |
|---|---|---|---|---|---|---|
| | Initial | 3 months | 0.5 month | 1 month | 1 month | 3 months |
| Description (Visual) | Off-white powder | Off-white slightly agglomerated powder | Gray paste, with soft consistency, quickly hardens upon trituration | Gray paste, with soft consistency, quickly hardens upon trituration | Off-white powder | Off-white agglomerated powder |
| Total Impurities | 0.44 | 0.48 | 0.40 | 0.41 | 0.49 | 0.43 |

Powder Flow Properties from Bulk/Tapped Density

The bulk and tapped density (BDTD) of final blends were determined using the USP <616> method using a Tapped density tester JV 1000, Copley Scientific). The bulk density was determined by measuring the volume of a known mass of powder sample in a graduated cylinder while the tapped density was measured by mechanically tapping the measuring cylinder until no further volume changes were observed. The powder flow properties were evaluated using the Carr's Compressibility Index (CI) and Hausner ratio (H) both derived using the measured values for bulk and tapped density as described below:

$$CI = (\text{Tapped density} - \text{Bulk density})/\text{Tapped density} \times 100\%$$

$$H = \text{Tapped density}/\text{Bulk density}$$

The values were interpreted as outlined in Table 6N.

TABLE 6N

Scale of Flowability

| Compressibility Index (%) | Flow Character | Hausner Ratio | Example |
|---|---|---|---|
| ≤10 | Excellent | 1.00-1.11 | Free-flowing granules |
| 11-15 | Good | 1.12-1.18 | Powdered granules |
| 16-20 | Fair | 1.19-1.25 | Coarse powders |
| 21-25 | Passable | 1.26-1.34 | Fine powders |
| 26-31 | Poor | 1.35-1.45 | Fluidizable powders |
| 32-37 | Very poor | 1.46-1.59 | Cohesive powders |
| ≥38 | Very, very poor | ≥1.60 | Very cohesive powders |

The bulk and tapped density of Formulations 6G (Placebo) and 6H were determined and the results are summarized in Table 6O. The physical properties of Compound 1 are such that the final BDTD for Formulation 6H is approximately two-fold less dense than Placebo Formulation 6G.

TABLE 6O

Density and Flow Properties of 6G and 6H

| | Density (g/cm³) | | Flow Properties | | |
|---|---|---|---|---|---|
| Lot No. | Bulk | Tapped | CI (%) | H | Flowability |
| 6G Sample 1 | 0.579 | 0.689 | 16 | 1.19 | Fair |
| 6G Sample 2 | 0.572 | 0.688 | 17 | 1.20 | Fair |

TABLE 6O-continued

Density and Flow Properties of 6G and 6H

| Lot No. | Density (g/cm³) | | Flow Properties | | |
| --- | --- | --- | --- | --- | --- |
| | Bulk | Tapped | CI (%) | H | Flowability |
| 6H Sample 1 | 0.287 | 0.368 | 22 | 1.28 | Passable |
| 6H Sample 2 | 0.288 | 0.364 | 21 | 1.26 | Passable |

Example 7: Organic Lipid Formulations

Formulation 7A

About 60 g solutol, 30 g TPGS, and 60 g PEG300 were added to a 250-mL glass vial while stirring at 700 rpm at 50° C. to obtain a clear vehicle solution. 4 g of Compound 1 Form $H^A$ (sifted through a 40-mesh sieve to form a fine powder) was added to 78 mL of vehicle solution heated to 50° C. The solution was stirred at 25° C. to form a homogeneously dispersed solution.

Formulation 7B

About 40 g Propyleneglycol, 40 g Labrasol, 10 g Pluronic F68, and 10 g water were added to a 250-mL glass vial while stirring at 700 rpm, under sonication, to obtain a clear vehicle solution. About 4 g of Compound 1 Form $H^A$ (sifted through a 40-mesh sieve to form a fine powder) was added to 40 mL of vehicle solution, and shaken by hand for 10 minutes. Additional vehicle solution was added to a total volume of 80 mL.

Formulation 7C

About 21 g Miglyol 812, 42 g Capmul MCM, 21 g Triacetin, and 56 g Cremophor EL were added to a 250-mL glass vial while stirring at 700 rpm, under sonication, to obtain a clear vehicle solution. About 4 g of Compound 1 Form $H^A$ (sifted through a 40-mesh sieve to form a fine powder) was added to 60 mL of vehicle solution, and was magnetically stirred for 10 minutes to form a uniform suspension. Additional vehicle solution was added to a total volume of 80 mL.

Formulation 7D

About 1 g methyl cellulose, 2 g Tween 80, and 197 g 0.01N HCl were added to a 250-mL glass vial while stirring at 700 rpm, under sonication, to obtain a clear vehicle solution. About 4 g of micronized Compound 1 Form $H^A$ powder was added to 60 mL of vehicle solution over 15 minutes, under magnetic stirring, to form a uniform suspension. Additional vehicle solution was added to a total volume of 80 mL and the pH was adjusted to 3.0 using 0.8 N NaOH.

Formulation 7E

About 1 g methyl cellulose, 2 g Tween 80, and 197 g 0.01N HCl were added to a 250-mL glass vial while stirring at 700 rpm, under sonication, to obtain a clear vehicle solution. About 4 g of micronized Compound 1 Form $H^B$ powder was added to 60 mL of vehicle solution over 20 minutes, under magnetic stirring, to form a uniform suspension. Additional vehicle solution was added to a total volume of 80 mL and the pH was adjusted to 3.0 using 0.8 N NaOH.

Formulation 7F

About 1 g methyl cellulose, 2 g Tween 80, and 197 g 0.01N HCl were added to a 250-mL glass vial while stirring at 700 rpm, under sonication, to obtain a clear vehicle solution. About 400 mg of micronized Compound 1 Form $H^A$ powder was added to 6 mL of vehicle solution over 10 minutes, under magnetic stirring, to form a uniform suspension. Additional vehicle solution was added to a total volume of 80 mL and the pH was adjusted to 3.0 using 0.8 N NaOH.

Formulation 7G

About 1 g methyl cellulose, 2 g Tween 80, and 197 g 0.01N HCl were added into 250-mL glass vial under stirring at 700 rpm and sonication to obtain a clear vehicle solution. About 60 mL of the vehicle solution was added to a 125-mL bottle. 4.49 g (calculated based on HPLC assay results) of sifted Compound 1 Form J powder was added to the bottle containing the vehicle solution in about 10 min under magnetic stirring to obtain a uniform suspension. Additional vehicle solution was added to a total volume of 80 mL and the pH was adjusted to 3.0 using 0.8 N NaOH.

Example 8: In Vivo Pharmacokinetic Data in Dogs

Animal Care

Fresh drinking water was available to all subjects, ad libitum. Subjects were fed twice daily. For PO dose groups, subjects were fed the afternoon (3:30-4:00 μm) prior to the day of dosing and the remaining food was removed at about 7:00 μm. Food was withheld until 4-hours post-dose.

Formulation

For studies using capsule formulations, the capsules were formulated as described in Examples 5 and 6.

For studies using non-capsule micronized blends, the formulation was prepared as a homogeneous opaque suspension/solution in water or aqueous solution. For example, Formulation 5B was accurately weighted into a glass vial and slowly mixed with water by continuous stirring. An appropriate amount of water was added to the dosing solution to reach the target dosing concentration. Stirring was applied until a homogeneous opaque suspension was obtained.

The concentration of Compound 1 in each suspension/solution formulation was confirmed by HPLC-UV or UPLC by collecting aliquots from the bottom, middle and top regions of the dosing solutions. All formulation samples were stored at ~2-8° C. until analyzed.

Administration

Subjects were fasted overnight through approximately 4 hours post-dosage. Subjects were weighted prior to dose administration on each day of dosing to calculate the actual dose volume. Subjects received a single oral gavage administration of the appropriate Formulation.

Blood Collection

Blood samples were collected pre-dose and post dosage at various time points. For example, in certain experiments, blood samples were collected at 0.25, 0.5, 1.0, 2.0, 4.0, 8.0, 16, 24, 30 and 48 hours post dosage. Approximately 0.5 mL of blood was collected at each time point via peripheral vessel from each subject. Blood samples were transferred into tubes containing potassium EDTA (0.85 mg-1.15 mg). Plasma samples were then prepared by centrifuging the blood samples at ~2-8° C., 3000 g for 10 minutes. One aliquot (about 200 μL) was collected for PK analysis and a second aliquot was collected for backup. All plasma samples were then frozen over dry ice and kept at −60° C. or lower until analysis.

Analysis

The plasma concentration of Compound 1 in each sample was determined by using the LC-MS/MS parameters reported below:

| Equipment | ACQUITY UPLC System |
|---|---|
| Analytical column | ACQUITY UPLC Protein BEH C4 300Å 1.7 μm 2.1 × 50 mm |
| Inject volume | 2 μL |
| Mobile phase A | 2 mM HCOONH$_4$ in water:acetonitrile (v:v, 95:5) |
| Mobile phase B | 2 mM HCOONH$_4$ in acetonitrile:water (v:v, 95:5) |
| Elution mode | Gradients (see below) |

| Gradient 1 | | | |
|---|---|---|---|
| Time (min) | Flow Rate (mL/min) | A % | B % |
| Initial | 0.65 | 85 | 15 |
| 1.2 | 0.65 | 5 | 95 |
| 1.4 | 0.65 | 5 | 95 |
| 1.41 | 0.65 | 85 | 15 |
| 1.6 | 0.65 | 85 | 15 |

| Gradient 2 | | | |
|---|---|---|---|
| Time (min) | Flow Rate (mL/min) | A % | B % |
| Initial | 0.65 | 80 | 20 |
| 0.8 | 0.65 | 65 | 35 |
| 1.2 | 0.65 | 5 | 95 |
| 1.4 | 0.65 | 5 | 95 |
| 1.41 | 0.65 | 80 | 20 |
| 1.6 | 0.65 | 80 | 20 |

| Mass spectrometer | Triple Quad 6500 Plus |
|---|---|
| Ionization mode | ESI(+) |
| Detective mode | MRM |

Plasma concentration data was subjected to a non-compartmental pharmacokinetic analysis using the Phoenix WinNonlin software (version 6.3, Pharsight, Mountain View, CA). The linear/log trapezoidal rule was applied in obtaining the PK parameters. Individual plasma concentration values that were below the lower limit of quantitation were excluded from the PK parameter calculation. All plasma concentrations and pharmacokinetic parameters were reported with three significant figures. The nominal dose levels and nominal sampling times were used in the calculation of all pharmacokinetic parameters.

Capsule Lots X8, X9

Three (3) non-naive male beagle dogs were dosed with Lots X8 and X9 (capsules containing Formulations 4A and 2A prepared as described in Examples 4 and 2 respectively), by once daily oral administration at a total target dosage of 30 mg/kg/day for Lot X8 and 125 mg/kg/day (100 mg/kg/day active) for Lot X9.

Before administration, there was a 4-day washout period to allow for clearance of Compound 1 from the test subjects from prior experiments. One subject dosed with Lot X9 had soft feces after dosing but otherwise, all subjects tolerated the administration with no adverse effects.

Results

TABLE 8A

Mean pharmacokinetic parameters of Compound 1 in male beagle dogs. Values reported as mean (std dev).

| Formulation/Lot | X8 | X9 |
|---|---|---|
| $C_{max}$ (ng/mL) | 662 (358) | 4887 (662) |
| $T_{max}$ (h) | 7.33 (7.57) | 14.9 (4.45) |
| $T_{1/2}$ (h) | 14.1 (17.0) | 13.4 (7.22) |

TABLE 8A-continued

Mean pharmacokinetic parameters of Compound 1 in male beagle dogs. Values reported as mean (std dev).

| Formulation/Lot | X8 | X9 |
|---|---|---|
| $AUC_{0-last}$ (h · ng/mL) | 9694 (6348) | 125752 (33162) |
| $AUC_{0-inf}$ (h · ng/mL) | 11812 (5926) | 154446 (66606) |

Capsule Lots X16A, X17, X21, Formulations 7A and 7G

Six (6) non-naive male beagle dogs were split into two groups of three subjects each. Group 1 was dosed with Capsule Lots X16A and X17 and lipid formulation 7A, and Group 2 was dosed with X21 and Formulation 7G, all at a target dose of 100 mg/kg/day of active compound via oral administration. X16A was administered as 5 capsules once daily, X17 was administered as 3 capsules once daily, X21 was administered as 11-12 capsules once daily, Formulation 7A was administered at a dosage of 1 mL/kg with a 50 mg/mL formulation, twice daily and Formulation 7G was administered at a dosage of 2 mL/kg with a 65 mg/mL formulation (50 mg/mL active) once daily.

Between each phase, there was a 3-day washout period to allow for clearance of Compound 1 from the test subjects. One subject administered Lot X17 had soft stool after dosing. All other subjects tolerated the administration with no adverse effects.

Results

TABLE 8B

Mean pharmacokinetic parameters of Compound 1 in male beagle dogs. Values reported as mean (std dev).

| Formulation/Lot | X16A | X17 | X21 |
|---|---|---|---|
| $C_{max}$ (ng/mL) | 4810 (3118) | 2483 (1301) | 3510 (530) |
| $T_{max}$ (h) | 18.7 (4.62) | 12.0 (6.93) | 1.67 (0.577) |
| $T_{1/2}$ (h) | 8.92 (10.4) | 3.00 (0.406) | 3.67 (0.532) |
| $AUC_{0-last}$ (h · ng/mL) | 126936 (125412) | 36448 (23123) | 37060 (10191) |
| $AUC_{0-inf}$ (h · ng/mL) | 162598 (187145) | 36466 (23143) | 37073 (10194) |

| Formulation/Lot | 7A | 7G |
|---|---|---|
| $C_{max}$ (ng/mL) | 6815 | 4853 (1053) |
| $T_{max}$ (h) | 9.00 | 9.33 (12.7) |
| $T_{1/2}$ (h) | 5.37 | 5.25 (1.88) |
| $AUC_{0-last}$ (h · ng/mL) | 148860 | 110204 (38027) |
| $AUC_{0-inf}$ (h · ng/mL) | 153132 | 112645 (40076) |

Capsule Lots X1, X2, X3, X4, X5, X6, X8 and Formulations 5B and 7E

Six (6) non-naive male beagle dogs were divided into two groups of three (3) animals/group. Group 1 was dosed with Capsule Lots X1 (200 mg/kg; 100 active), X3 (200 mg/kg; 100 active), and X5 (250 mg/kg; 100 active), each prepared as described in Example 5 herein, by once daily oral administration. Group 2 was dosed with Capsule Lots X2 (200 mg/kg; 100 active), X4 (200 mg/kg; 100 active), X6 (250 mg/kg; 100 active), X2 again (200 mg/kg; 100 active), X8 (100 mg/kg), a suspension of Formulation 5B in water (200 mg/kg; 100 active; dose concentration of 100 mg/mL; 50 active), and Formulation 7E (100 mg/kg; 50 mg/mL dose concentration), each prepared as described in Examples 5 and 7 herein, by once daily oral administration. X1-X6 were dosed as 6-8 capsules based on subject weight, X8 was dosed as 3 capsules and the suspension formulations were dosed at 2 mL/kg.

Between each phase, there was a 3-day washout period to allow for clearance of Compound 1 from the test subjects. One subject in each study dosed with X5, X6 and X8 had liquid or soft stool after dosing and one subject dosed with the suspension of Formulation 5B had soft stool and minor vomiting. All other subjects tolerated the administration with no adverse effects.

Results

TABLE 8C

Mean pharmacokinetic parameters of Compound 1 in male beagle dogs. Values reported as mean (std dev).

| Formulation/ Lot | X1 | X2-experiment 1 | X2-experiment 2 | X3 |
|---|---|---|---|---|
| $C_{max}$ (ng/mL) | 4507 (2577) | 3267 (929) | 5113 (1699) | 4223 (1982) |
| $T_{max}$ (h) | 12.7 (9.45) | 8.00 (10.4) | 8.00 (10.4) | 14.0 (10.4) |
| $T_{1/2}$ (h) | 4.12 (0.418) | 5.78 (1.57) | 6.92 (4.27) | 7.32 (3.31) |
| $AUC_{0-last}$ (h · ng/mL) | 75430 (49377) | 48387 (18608) | 88443 (81889) | 74336 (50997) |
| $AUC_{0-inf}$ (h · ng/mL) | 757701 (49572) | 49452 (19631) | 96860 (96304) | 79171 (57406) |

| Formulation/ Lot | X4 | X5 | X6 | X8 |
|---|---|---|---|---|
| $C_{max}$ (ng/mL) | 2421 (1469) | 4327 (2401) | 5823 (672) | 704 (143) |
| $T_{max}$ (h) | 4.00 (3.46) | 10.7 (8.33) | 2.00 (0.00) | 1.67 (0.577) |
| $T_{1/2}$ (h) | 6.91 (2.54) | 5.49 (1.67) | 4.84 (2.22) | 7.81 (4.76) |
| $AUC_{0-last}$ (h · ng/mL) | 35636 (33287) | 92321 (59063) | 74893 (23.03) | 8045 (2690) |
| $AUC_{0-inf}$ (h · ng/mL) | 37069 (35434) | 93912 (60434) | 75330 (1686) | 8216 (2543) |

| Formulation/ Lot | 5B | 7E |
|---|---|---|
| $C_{max}$ (ng/mL) | 4840 (2397) | 3247 (1459) |
| $T_{max}$ (h) | 11.3 (9.02) | 7.67 (10.7) |
| $T_{1/2}$ (h) | 10.2 (6.33) | 8.83 (4.15) |
| $AUC_{0-last}$ (h · ng/mL) | 109933 (77682) | 61283 (58500) |
| $AUC_{0-inf}$ (h · ng/mL) | 130559 (109727) | 69468 (72085) |

Capsule Lots X10, X11, X12, X13, X14, X15, and X16B

Three (3) non-naive male beagle dogs were dosed with Capsule Lots X10 (20 mg/kg; 10 active), X11 (20 mg/kg; 10 active), X12 (20 mg/kg; 10 active), X13 (20 mg/kg; 10 active), X14 (20 mg/kg; 10 active), X15 (20 mg/kg; 10 active), and X16B (10 mg/kg) each prepared as described in Example 6 herein, by once daily oral administration. Each dog was dosed with 1 capsule, as determined by subject weight.

Each subject was administered pentagastrin (0.25 mg/mL and 0.024 mL/kg) at 6 pg/kg by intramuscular injection, approximately 30 minutes before administration of the Compound 1 dosages. The pentagastrin served to lower stomach pH of the subjects, to better mimic human stomach pH. Between each phase, there was a 3-day washout period to allow for clearance of Compound 1 from the test subjects. All subjects tolerated the administration with no adverse effects.

Results

TABLE 8D

Mean pharmacokinetic parameters of Compound 1 in male beagle dogs. Values reported as mean (std dev).

| Formulation/ Lot | X10 | X11 | X12 | X13 |
|---|---|---|---|---|
| $C_{max}$ (ng/mL) | 2317 (850) | 1857 (741) | 1717 (571) | 2433 (328) |
| $T_{max}$ (h) | 2.00 (0) | 6.67 (8.08) | 4.67 (3.06) | 2.00 (0) |
| $T_{1/2}$ (h) | 4.08 (1.88) | 3.70 (1.08) | 4.04 (1.21) | 3.77 (1.44) |
| $AUC_{0-last}$ (h · ng/mL) | 27165 (15575) | 18650 (6303) | 21086 (6262) | 26040 (3425) |
| $AUC_{0-inf}$ (h · ng/mL) | 27385 (15751) | 18689 (6344) | 21160 (6375) | 26162 (3419) |

| Formulation/ Lot | X14 | X15 | X16B |
|---|---|---|---|
| $C_{max}$ (ng/mL) | 1263 (429) | 1987 (478) | 2095 (1017) |
| $T_{max}$ (h) | 2.00 (0) | 2.00 (0) | 5.33 (5.77) |
| $T_{1/2}$ (h) | 3.91 (1.31) | 2.82 (1.45) | 4.03 (1.70) |
| $AUC_{0-last}$ (h · ng/mL) | 12582 (824) | 16786 (2901) | 28374 (13539) |
| $AUC_{0-inf}$ (h · ng/mL) | 12679 (709) | 16820 (2881) | 28589 (13741) |

Formulations 7A, 7B, 7C and 7D

Three (3) non-naive male beagle dogs were dosed with Formulations 7A, 7B, 7C and 7D, each prepared as described in Example 7 herein, by once daily oral administration. The Formulations were dosed at 2 mL/kg of a 50 mg/mL solution for a total target dose of 100 mg/kg of Compound 1.

Between each phase, there was a 3-day washout period to allow for clearance of Compound 1 from the test subjects. One subject in each study dosed with Formulations 7A and 7C had liquid or soft stool after dosing, a different subject dosed with Formulation 7A exhibited excessive salivation and a different subject administered with Formulation 7C produced a small amount of vomit. All other subjects tolerated the administration with no adverse effects.

Results

TABLE 8E

Mean pharmacokinetic parameters of Compound 1 in male beagle dogs. Values reported as mean (std dev).

| Formulation/ Lot | 7A | 7B | 7C | 7D |
|---|---|---|---|---|
| $C_{max}$ (ng/mL) | 16100 (9093) | 4943 (1076) | 8033 (2560) | 6617 (2839) |
| $T_{max}$ (h) | 3.00 (1.73) | 10.7 (11.5) | 3.33 (1.15) | 11.3 (11.4) |
| $T_{1/2}$ (h) | 6.96 (5.73) | 4.08 (0.749) | 3.80 (0.977) | 4.89 (3.30) |
| $AUC_{0-last}$ (h · ng/mL) | 283384 (211700) | 84927 (34648) | 128298 (52870) | 151260 (100212) |
| $AUC_{0-inf}$ (h · ng/mL) | 304360 (247385) | 85294 (35200) | 128418 (52903) | 157254 (109966) |

Example 9: Micronization of Compound 1 HCl Form I

Sample Preparation and Characterization

HCl salt Form I of Compound 1 was prepared as a micronized powder by adding 30 g of the salt (prepared as described in the Materials and Methods section) to the injector of a jetmill, stepwise, and micronizing using an injector gas pressure of 4 bar for 1 hour. The micronized HCl salt powder was collected (86.3% yield, as an off-white powder) and analyzed by PLM, XRPD, PSD, GC and HPLC. The XRPD pattern for the micronized HCl salt Form I of Compound 1 matched the crystalline pattern for the unmilled Form I starting material. The particle size distribution analysis showed a $D_{10}$=0.62 m, $D_{50}$=1.65 m, and $D_{90}$=3.75 m. The water content was measured to be 0.343%, which was a slight increase over the unmilled starting material (0.184%), which could be attributed to an increase in hygroscopicity inherent to a decreased particle size/increased surface area. Ion chromatography analysis of the micronized powder showed the molar ratio of HCl to Compound 1 was about 0.85:1, similar to the unmilled starting material. Residual isopropanol content was measured as 3336 ppm via gas chromatography. HPLC measurements determined that the micronized HCl salt had a purity of 99.80%, which was nearly identical to the unmilled starting material (99.77%). The micronized HCl salt Form I of Compound 1, without any additional excipients or additives, is denoted as Formulation 9A.

the citric acid (granular grade) was ground using a mortar with pestle and sieved with 60 mesh (250 μm) before weighing, thereby generating citric acid with a reduced average particle size (designated as fine granular "FG" citric acid below). The other powders were screened together through a 30 mesh sieve and mixed for 2.5 min at 25 rpm using a V-blender. This mixture was again screened through a 30 mesh sieve and returned to the V-blender to be mixed for another 2.5 min. The blend was split in two portions (20 and 40 g). The 20 g were directly encapsulated. The other 40 g was roller compacted.

The roller compaction of the 40 g portion of Formulation 10C was performed using a Vector TFC-Labo. The blend adhered/stuck to the rolls at all operational parameters tested. Although no uniform/regular ribbons formed, the compacted material was recovered by scraping with a spatula and screened through a 20 mesh (850 μm) sieve. Addition of magnesium stearate to generate Formulation 10D (Table 10D) greatly improved processing.

TABLE 9A

Characterization of micronized HCl salt of Compound 1

| Formulation | Yield | XRPD | Water content (%) | $D_{10}$ (μm) | | $D_{50}$ (μm) | | $D_{90}$ (μm) | | Salt ratio (IC) | HPLC test Purity (%) |
|---|---|---|---|---|---|---|---|---|---|---|---|
| 9A | 86.3% | No form change | 0.343 | 1 | 0.63 | 1 | 1.67 | 1 | 3.80 | 0.85 (acid/FB) | 99.80 |
|  |  |  |  | 2 | 0.62 | 2 | 1.63 | 2 | 3.67 |  |  |
|  |  |  |  | 3 | 0.62 | 3 | 1.66 | 3 | 3.78 |  |  |
|  |  |  |  | Avg. | 0.62 | Avg. | 1.65 | Avg. | 3.75 |  |  |

1-Week and 4-Week Stability Studies of Formulation 9A

Figure 6:
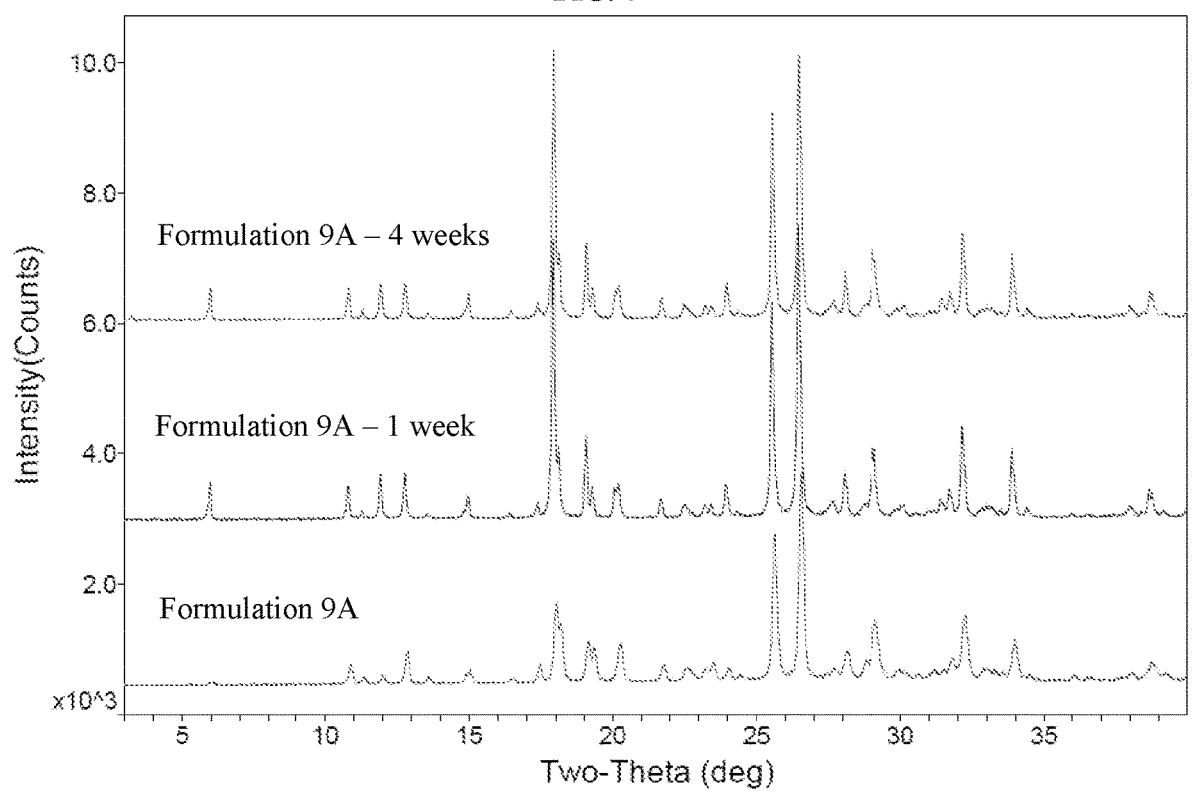
FIG. 6 depicts XRPD patterns for micronized Compound 1 HCl salt Form I Formulation 9A after 1 week and 4 weeks stored at 25° C. and 60% relative humidity, as compared to Formula 9A before the stability study.

The chemical and physical stability of the micronized Formulation 9A was studied by placing the material in a 40-mL glass vial, covered by aluminum foil with pinholes and stored open under 25° C./60% RH for 1 week and 4 weeks. PLM and XRPD (FIG. 6) patterns for Formulation 9A stored under 25° C./60% RH (open) for 1 week and 4 weeks both showed that the Compound 1 HCl salt material remained crystalline with the same pattern as the Form I starting material. The particle size distribution results showed comparable $D_{50}$ after 1 week and 4 weeks as the initial sample. The purity HPLC results showed almost no change, indicating that the micronized powder form of HCl salt Form I was chemically stable.

Example 10: Additional Blended Formulations of Compound 1 Form $H^4$ and Related Placebo Formulations Additional Dry Blend Formulations Placebo Formulation 10A (Table 10A) and Compound 1 Form $H^4$ Formulation 10B (Table 10B) blends were prepared at 500 and 100 g batch size, respectively, to evaluate scale-up feasibility. For these blends, the powders were screened through a 35 mesh (500 μm) sieve and mixed for 5 min using a V-blender at 25 rpm.

Formulation 10C (Table 10C) was prepared using micronized Compound 1 Form $H_4$. To improve blend uniformity and homogeneity with micronized Compound 1 Form $H_4$,

TABLE 10A

Composition of Placebo Formulation 10A

| Ingredient | % w/w | g/batch |
|---|---|---|
| Microcrystalline cellulose 102 | 50 | 250 |
| Citric acid anhydrous FG/Acidulant | 45 | 225 |
| Sodium lauryl sulfate/Surfactant | 5 | 25 |
| Total: | 100 | 500 |

TABLE 10B

Composition of Compound 1 Formulation 10B

| Ingredient | % w/w | g/batch |
|---|---|---|
| Compound 1 Form $H^4$/API | 50 | 50 |
| Citric acid anhydrous FG/Acidulant | 45 | 45 |
| Sodium lauryl sulfate/Surfactant | 5 | 5 |
| Total: | 100 | 100 |

TABLE 10C

Composition of Compound 1 Formulation 10C

| Ingredient | % w/w | g/batch |
|---|---|---|
| Compound 1 Form H$^4$/API | 50 | 30 |
| Citric acid anhydrous FG*/Acidulant | 45 | 27 |
| Sodium lauryl sulfate/Surfactant | 5 | 3 |
| Total: | 100 | 60 |

*Ground/screened (60 mesh) by hand

TABLE 10D

Composition of Compound 1 Formulation 10D

| Ingredient | % w/w | g/batch |
|---|---|---|
| Formulation 10C | 99 | 70 |
| Magnesium stearate grade MF-3-V/Lubricant | 1 | 0.7 |
| Total: | 100 | 70.7 |

Formulation 10E was prepared by using a combination of citric acid anhydrous fine granular (FG) and citric acid anhydrous powder (P) to match the PSD that would be comparable to the ground 60 mesh used for Formulation 10C. Different combinations of FG and P were prepared and analyzed by particle size distribution (PSD) and bulk density/tapped density (BDTD), and a mixture of FG/P 35:10 was selected because the particle size distribution most closely matched that of the ground and screened citric acid used in Formulation 10C. The sodium lauryl sulfate was introduced alone into the blender for 0.5 minutes to coat the internal walls. The other powders and SLS from the blender were then screened together using a 35 mesh (500 µm) sieve and mixed, as was done for Formulation 10C. A new placebo Formulation 10F (Table 10F) was also formulated with both granular and powdered anhydrous citric acid, as a direct comparison to Formulation 10E.

TABLE 10E

Composition of Compound 1 Formulation 10E

| Ingredient | % w/w | g/batch |
|---|---|---|
| Compound 1 Form H$^4$/API | 50 | 10 |
| Citric acid anhydrous fine granular | 35 | 7 |
| Citric acid anhydrous powder | 10 | 2 |
| Sodium lauryl sulfate | 5 | 1 |
| Total: | 100 | 20 |

TABLE 10F

Composition of Placebo Formulation 10F

| Ingredient | % w/w | g/batch |
|---|---|---|
| Microcrystalline cellulose 102 | 50 | 50 |
| Citric acid anhydrous fine granular | 25 | 25 |
| Citric acid anhydrous powder | 20 | 20 |
| Sodium lauryl sulfate | 5 | 5 |
| Total: | 100 | 100 |

The final blends were filled into gelatin capsules at different drug dose as shown in Table 10G.

TABLE 10G

Compound 1 Form H$^4$ Capsules

| Lot No. | Formulation | API Dose (mg) | Preparation |
|---|---|---|---|
| X22 | 10B | 3 | 6 mg blend in size 3 Gelatin capsules |
| X23 | 10B | 50 | 100 mg blend in size 1 Gelatin capsules |
| X24 | 10B | 125 | 250 mg blend in size 0 Gelatin capsules |
| X25 | 10C | 3 | 6 mg blend in size 3 Gelatin capsules |
| X26 | 10C | 50 | 100 mg blend in size 1 Gelatin capsules |
| X27 | 10C | 100 | 200 mg blend in size 0 Gelatin capsules |
| X28 | 10C | 3 | 6 mg blend in size 3 Gelatin capsules |
| X29 | 10C | 50 | 100 mg blend in size 1 Gelatin capsules |
| X30 | 10C | 100 | 200 mg blend in size 0 Gelatin capsules |
| X31 | 10E | 3 | 6 mg blend in size 3 Gelatin capsules |
| X32 | 10E | 50 | 100 mg blend in size 1 Gelatin capsules |
| X33 | 10E | 100 | 200 mg blend in size 0 s Gelatin capsule |

Example 11: In Vivo Pharmacokinetic Studies in Dogs, Utilizing Micronized HCl Salt Form Animal Care The room where the animals were kept was controlled and monitored for relative humidity (targeted mean range 40% to 70%) and temperature (targeted mean range 18 to 26° C., and any excursion from this range will be documented as a deviation) with 10 to 20 air changes/hour. The room was kept on a 12-hour light/dark cycle except when interruptions were necessitated by study activities.

Animals were pair-housed in cages that are in accordance with applicable animal welfare laws and regulations during the acclimation period. The dogs were individually housed in cages for the duration of the experiment. Reverse osmosis water was available to the animals, ad libitum. Enrichment toys were also provided.

Animals were fed twice daily, approximately 220 grams of Certified Dog Diet daily (certified vendor). These amounts were adjusted as necessary based on food consumption of the group or an individual body weight change.

Animals were fed the afternoon (at 3:30 to 4:00 µm) prior to the day of oral dosing and the remaining food was removed at 7:00 µm. On the day of dosing, food was withheld until 2-hour post-dose unless specified in the protocol. Animals were fed once on the day of dosing, at an amount of approximately 220 grams of food.

Formulations

Capsule formulations were prepared using Compound 1 HCl salt Form I, in unmilled form as prepared according to the Materials and Methods section and as micronized Formulation 9A, and using micronized free base Formulations 10D and 10E. An aqueous suspension formulation was also prepared using Formulation 10E, prepared in an analogous manner as that described in Example 8. A summary of the formulations used in this study is described below in Table 11A.

TABLE 11A

Pharmacokinetic study formulation overview

| Lot # | Formulation | Dosing Form | Target Dose |
|---|---|---|---|
| X34 | Compound 1 HCl salt Form I, unmilled, no additional components | Powder-in-capsule | 11 mg/kg (10 mg/kg Compound 1) 1 capsule per dose |
| X35 | 9A | Powder-in-capsule | 11 mg/kg (10 mg/kg Compound 1) 1 capsule per dose |
| X36 | 10E | Powder-in-capsule | 20 mg/kg (10 mg/kg Compound 1) 1 capsule per dose |
| X37 | 10E | Aqueous suspension | 20 mg/kg (10 mg/kg Compound 1) 2 mg/mL (1 mg/mL Compound 1) Dose volume: 10 mL/kg |
| X38 | 10D | Powder-in-capsule | 20 mg/kg (10 mg/kg Compound 1) 1 capsule per dose |

Administration

Subjects were fasted overnight through approximately 2 hours post-dosage. Subjects were weighted prior to dose administration on each day of dosing to calculate the actual dose volume. Subjects received a single oral gavage administration of the appropriate Formulation.

Blood Collection

Blood samples were collected pre-dose and post dosage at various time points. Blood samples were collected at 0.25, 0.5, 1.0, 2.0, 4.0, 8.0, 12, 16, 20 24, 30 and 48 hours post dosage. Approximately 0.25 mL of blood was collected at each time point via peripheral vessel from each subject. Blood samples were transferred into tubes containing potassium EDTA (0.85 mg-1.15 mg). Plasma samples were then prepared by centrifuging the blood samples at ~2-8° C., 3200 g for 10 minutes, within 1 hour of collection. A plasma sample (about 0.1 mL) was collected in a polypropylene micro-centrifuge tube and stored as a backup. All plasma samples were frozen over dry ice and kept at −60° C. or lower until analysis.

Analysis

Sample and data analysis were conducted as reported in Example 8.

Capsule Lots X34, X35, X36, and X38, and Suspension X37

Three male beagle dogs were dosed with capsule Lots X34, X35, X36, and X38 (capsules containing Compound 1 HCl salt Form I, unmilled, Formulation 9A, Formulation 10E, and Formulation 10D respectively, as described in Table 11A), and suspension Lot X37 (aqueous suspension containing Formulation 10E, as described in Table 11A) by once daily oral administration at a total target Compound 1 dosage of 10 mg/kg/day.

Each subject was administered pentagastrin (0.25 mg/mL and 0.024 mL/kg) at 6 µg/kg by intramuscular injection, approximately 30 minutes before administration of the Compound 1 dosages. The pentagastrin served to lower stomach pH of the subjects, to better mimic human stomach pH. Before administration, there was a 3-day washout period to allow for clearance of Compound 1 from the test subjects from prior experiments. No adverse effects were observed in the subjects.

Results

TABLE 11B

Mean pharmacokinetic parameters of Compound 1 in male beagle dogs. Values reported as mean (std dev).

| Formulation/Lot | X34 | X35 | X36 | X37 | X38 |
|---|---|---|---|---|---|
| $C_{max}$ (ng/mL) | 2627 (1225) | 2977 (498) | 2000 (711) | 2447 (466) | 1282 (971) |
| $T_{max}$ (h) | 2.00 (0) | 2.00 (0) | 1.67 (0.577) | 1.33 (0.577) | 1.50 (0.866) |
| $T_{1/2}$ (h) | 3.59 (1.70) | 5.09 (1.02) | 4.02 (1.54) | 3.36 (1.54) | 4.55 (3.51) |
| $AUC_{0-last}$ (h · ng/mL) | 24928 (9912) | 27477 (5003) | 18685 (8632) | 19968 (1111) | 9524 (6237) |
| $AUC_{0-inf}$ (h · ng/mL) | 24969 (9905) | 27600 (5080) | 18763 (8694) | 19979 (1103) | 9620 (6252) |

Those skilled in the art will recognize, or be able to ascertain, using no more than routine experimentation, numerous equivalents to the specific compositions and procedures described herein. Such equivalents are considered to be within the scope of this disclosure, and are covered by the following claims.

What is claimed is:

1. A pharmaceutical composition comprising:
   (i) N-(5-(5-((1R,2S)-2-fluorocyclopropyl)-1,2,4-oxadiazol-3-yl)-2-methylphenyl)imidazo[1,2-a]pyridine-3-carboxamide in the form of microparticles comprising free base Form $H^4$ in an amount of about 35 wt % to about 55 wt %;
   (ii) an acidulant, wherein the acidulant is citric acid, or a salt thereof, in an amount of about 5 wt % to about 50 wt %;
   (iii) a surfactant, wherein the surfactant is sodium dodecyl sulfate (SDS) in an amount of about 1 wt % to about 20 wt %; and
   optionally one or more of: a filler, a disintegrant, a lubricant, a glidant, a stabilizer, a coloring agent, a sweetener and a flavorant.

2. The pharmaceutical composition of claim 1, wherein the pharmaceutical composition is a micronized powder blend comprising N-(5-(5-((1R,2S)-2-fluorocyclopropyl)-1,2,4-oxadiazol-3-yl)-2-methylphenyl)imidazo[1,2-a]pyridine-3-carboxamide in the form of microparticles comprising free base Form $H^4$.

3. The pharmaceutical composition of claim 2, wherein free base Form $H^4$ of N-(5-(5-((1R,2S)-2-fluorocyclopropyl)-1,2,4-oxadiazol-3-yl)-2-methylphenyl)imidazo[1,2-a]pyridine-3-carboxamide is a crystalline solid form having peaks in its X-ray powder diffraction pattern selected at about 12.8, about 13.6, and about 19.3 degrees 2-theta.

4. The pharmaceutical composition of claim 1, wherein the acidulant is anhydrous citric acid.

5. The pharmaceutical composition of claim 1, wherein the acidulant is citric acid, in the form of microparticles having a median particle size ($D_{50}$) of about 200 µm to about 300 µm.

6. The pharmaceutical composition of claim 1, wherein the pharmaceutical composition comprises:
(i) N-(5-(5-((1R,2S)-2-fluorocyclopropyl)-1,2,4-oxadiazol-3-yl)-2-methylphenyl)imidazo[1,2-a]pyridine-3-carboxamide in the form of crystalline free base Form $H^4$ microparticles, in an amount of about 35 wt % to about 55 wt %;
(ii) anhydrous citric acid in an amount of about 5 wt % to about 50 wt %; and
iii) SDS in an amount of about 1 wt % to about 20 wt %.

7. The pharmaceutical composition of claim 1, wherein the pharmaceutical composition comprises:
(i) N-(5-(5-((1R,2S)-2-fluorocyclopropyl)-1,2,4-oxadiazol-3-yl)-2-methylphenyl)imidazo[1,2-a]pyridine-3-carboxamide in the form of crystalline free base Form $H^4$ microparticles, in an amount of about 45 wt % to about 50 wt %;
ii) anhydrous citric acid in an amount of about 10 wt % to about 45 wt %; and
(iii) SDS in an amount of about 5 wt % to about 15 wt %.

8. The pharmaceutical composition of claim 1, wherein the pharmaceutical composition comprises:
(i) N-(5-(5-((1R,2S)-2-fluorocuclopropyl)-1,2,4-oxadiazol-3-yl)-2-methylphenyl)imidazo[1,2-a]pyridine-3-carboxamide in the form of crystalline free base Form $H^4$ microparticles, in an amount of about 50 wt %;
(ii) anhydrous citric acid in an amount of about 45 wt %; and
(iii) SDS in an amount of about 5 wt %.

9. The pharmaceutical composition of claim 1, wherein the N-(5-(5-((1R,2S)-2-fluorocyclopropyl)-1,2,4-oxadiazol-3-yl)-2-methylphenyl)imidazo[1,2-a]pyridine-3-carboxamide is in the form of crystalline free base Form $H^4$ microparticles having a median particle size ($D_{50}$) of about 1.0 µm to about 2.0 µm and a span less than about 3.

10. The pharmaceutical composition of claim 1, wherein the pharmaceutical composition is formulated as a capsule appropriate for oral administration.

11. A method of inhibiting the activity of a c-kit kinase in a patient, comprising administering to said patient a pharmaceutical composition according to claim 1.

12. The method of claim 11, wherein the pharmaceutical composition is administered to the patient orally.

* * * * *